US006790178B1

(12) United States Patent
Mault et al.

(10) Patent No.: US 6,790,178 B1
(45) Date of Patent: Sep. 14, 2004

(54) PHYSIOLOGICAL MONITOR AND ASSOCIATED COMPUTATION, DISPLAY AND COMMUNICATION UNIT

(75) Inventors: James R. Mault, Evergreen, CO (US); Noel Johnson, Saratoga, CA (US); John Sanderson, Bainbridge Island, WA (US)

(73) Assignee: Healthetech, Inc., Golden, CO (US)

( * ) Notice: Subject to any disclaimer, the term of this patent is extended or adjusted under 35 U.S.C. 154(b) by 278 days.

(21) Appl. No.: 09/669,125

(22) Filed: Sep. 25, 2000

Related U.S. Application Data

(60) Provisional application No. 60/155,851, filed on Sep. 24, 1999, provisional application No. 60/158,553, filed on Oct. 8, 1999, provisional application No. 60/158,556, filed on Oct. 8, 1999, provisional application No. 60/158,554, filed on Oct. 8, 1999, provisional application No. 60/159,285, filed on Oct. 13, 1999, provisional application No. 60/165,166, filed on Nov. 12, 1999, provisional application No. 60/165,988, filed on Nov. 17, 1999, provisional application No. 60/167,276, filed on Nov. 24, 1999, provisional application No. 60/177,011, filed on Jan. 19, 2000, provisional application No. 60/177,016, filed on Jan. 19, 2000, provisional application No. 60/177,009, filed on Jan. 19, 2000, provisional application No. 60/178,979, filed on Jan. 28, 2000, provisional application No. 60/179,882, filed on Feb. 2, 2000, provisional application No. 60/194,126, filed on Apr. 3, 2000, provisional application No. 60/201,902, filed on May 4, 2000, provisional application No. 60/195,779, filed on Apr. 10, 2000, provisional application No. 60/205,709, filed on May 19, 2000, provisional application No. 60/206,905, filed on May 25, 2000, provisional application No. 60/207,089, filed on May 25, 2000, provisional application No. 60/207,051, filed on May 25, 2000, provisional application No. 60/209,921, filed on Jun. 7, 2000, provisional application No. 60/212,319, filed on Jun. 16, 2000, provisional application No. 60/219,069, filed on Jul. 18, 2000, provisional application No. 60/219,070, filed on Jul. 18, 2000, provisional application No. 60/224,651, filed on Aug. 11, 2000, provisional application No. 60/225,101, filed on Aug. 14, 2000, provisional application No. 60/225,454, filed on Aug. 15, 2000, provisional application No. 60/228,388, filed on Aug. 28, 2000, provisional application No. 60/234,866, filed on Sep. 22, 2000, and provisional application No. 60/234,154, filed on Sep. 21, 2000.

(51) Int. Cl.[7] .................................................. A61B 5/00
(52) U.S. Cl. ........................ 600/300; 128/903; 128/920; 600/508
(58) Field of Search .................................. 600/300–301, 600/500–509, 549, 587–595; 128/903, 904, 120; 374/100

(56) References Cited

U.S. PATENT DOCUMENTS 2,630,798 A * 3/1953 White et al. ................ 128/2.07

(List continued on next page.)

FOREIGN PATENT DOCUMENTS

DE          198 10 476       9/1998

(List continued on next page.)

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise."

(List continued on next page.)

Primary Examiner—Max F. Hindenburg
Assistant Examiner—Michael Astorino
(74) Attorney, Agent, or Firm—Cooley Godward LLP

(57) ABSTRACT

Various physiological monitor modules are provided for use with computing devices such as personal digital assistants (PDAs). In some embodiments, the personal digital assistant provides the controls, display, and processing circuitry for the physiological monitor module. The personal digital assistant stores data from the physiological monitors so that the data may be used in various software applications. In other embodiments, the physiological monitor and the personal digital assistant include accessory slots sized to accept memory modules which may be used to transfer data therebetween. In yet other embodiments, the physiological monitors include data storage but do not include onboard processing capability, and data is transferred to a personal digital assistant either during or after use of the physiological monitor.

1 Claim, 15 Drawing Sheets

U.S. PATENT DOCUMENTS

| | | | |
|---|---|---|---|
| 2,826,912 A | 3/1958 | Kritz | 73/194 |
| 2,831,348 A | 4/1958 | Kritz | 73/861.28 |
| 2,838,399 A * | 6/1958 | Vogel, Jr. | 99/48 |
| 2,869,357 A | 11/1959 | Kritz | 73/32 |
| 2,911,825 A | 11/1959 | Kritz | 73/194 |
| 2,920,012 A * | 1/1960 | Sanders et al. | |
| 3,213,684 A * | 10/1965 | Seaton et al. | 73/190 |
| 3,220,255 A | 11/1965 | Scranton et al. | 73/204 |
| 3,250,270 A * | 5/1966 | Bloom | 128/2.07 |
| 3,306,283 A | 2/1967 | Arp | 128/2.07 |
| 3,523,529 A * | 8/1970 | Kissen | 128/2.07 |
| 3,527,205 A | 9/1970 | Jones | 128/2.08 |
| 3,681,197 A * | 8/1972 | Smith | 195/63 |
| 3,726,270 A * | 4/1973 | Griffis et al. | 128/2.08 |
| 3,797,480 A * | 3/1974 | Williams | 128/2.08 |
| 3,799,149 A | 3/1974 | Rummel et al. | 128/2.07 |
| 3,814,091 A | 6/1974 | Henkin | 128/188 |
| 3,834,375 A | 9/1974 | Sanctuary et al. | 128/2.07 |
| 3,895,630 A | 7/1975 | Bachman | 128/2.07 |
| 3,938,551 A | 2/1976 | Henkin | 137/613 |
| 3,962,917 A | 6/1976 | Terada | 73/204 |
| 3,967,690 A | 7/1976 | Northcutt | 177/25 |
| 3,972,038 A | 7/1976 | Fletcher et al. | |
| 3,991,304 A | 11/1976 | Hillsman | 235/151.33 |
| 4,003,396 A | 1/1977 | Fleischmann | 137/83 |
| 4,008,712 A | 2/1977 | Nyboer | |
| 4,051,847 A | 10/1977 | Henkin | 128/145.6 |
| 4,078,554 A | 3/1978 | LeMaitre et al. | 128/2.08 |
| 4,100,401 A | 7/1978 | Tutt et al. | |
| 4,101,071 A | 7/1978 | Brejnik et al. | |
| 4,113,039 A | 9/1978 | Ozaki et al. | 177/25 |
| 4,117,834 A | 10/1978 | McPartland et al. | |
| 4,151,668 A | 5/1979 | Hungerford | 40/495 |
| 4,159,416 A | 6/1979 | Brejnik et al. | |
| 4,186,735 A | 2/1980 | Henneman et al. | 128/201.25 |
| 4,188,946 A | 2/1980 | Watson et al. | 128/204.22 |
| 4,192,000 A | 3/1980 | Lipsey | 364/415 |
| 4,197,857 A | 4/1980 | Osborn | 600/531 |
| 4,200,094 A | 4/1980 | Gedeon et al. | 128/201.13 |
| 4,211,239 A | 7/1980 | Raemer et al. | |
| 4,212,079 A | 7/1980 | Segar et al. | 364/900 |
| 4,221,224 A | 9/1980 | Clark | |
| 4,221,959 A | 9/1980 | Sessler | 377/13 |
| 4,224,952 A | 9/1980 | Sidorenko et al. | |
| 4,230,108 A | 10/1980 | Young | |
| 4,244,020 A | 1/1981 | Ratcliff | 364/413 |
| 4,318,447 A | 3/1982 | Northcutt | 177/25 |
| 4,321,674 A | 3/1982 | Krames et al. | 364/413 |
| 4,341,867 A | 7/1982 | Johansen | 435/189 |
| 4,353,375 A | 10/1982 | Colburn et al. | |
| 4,359,057 A | 11/1982 | Manzella | |
| 4,366,873 A | 1/1983 | Levy et al. | 177/25 |
| 4,368,740 A | 1/1983 | Binder | |
| 4,380,802 A | 4/1983 | Segar et al. | 364/900 |
| 4,386,604 A | 6/1983 | Hershey | |
| 4,387,777 A | 6/1983 | Ash | 177/43 |
| 4,423,792 A | 1/1984 | Cowan | 177/25 |
| 4,425,805 A | 1/1984 | Ogura et al. | 73/861.29 |
| 4,440,177 A | 4/1984 | Anderson et al. | 600/532 |
| 4,444,201 A | 4/1984 | Itoh | |
| 4,463,764 A | 8/1984 | Anderson et al. | 600/532 |
| 4,566,461 A | 1/1986 | Lubell et al. | 128/668 |
| 4,571,682 A | 2/1986 | Silverman et al. | 364/413 |
| 4,572,208 A | 2/1986 | Cutler et al. | |
| 4,575,804 A | 3/1986 | Ratcliff | 364/715 |
| 4,577,710 A | 3/1986 | Ruzumna | 177/245 |
| 4,598,700 A | 7/1986 | Tamm | |
| 4,608,995 A | 9/1986 | Linnarsson et al. | |
| 4,619,269 A | 10/1986 | Cutler et al. | |
| 4,629,015 A | 12/1986 | Fried et al. | 177/25 |
| 4,648,396 A | 3/1987 | Raemer | 600/534 |
| 4,650,218 A | 3/1987 | Hawke | 283/67 |
| 4,658,832 A | 4/1987 | Brugnoli | 600/532 |
| 4,686,624 A | 8/1987 | Blum et al. | 364/415 |
| 4,709,331 A | 11/1987 | Barkett et al. | 364/413 |
| 4,731,726 A | 3/1988 | Allen, III | 364/416 |
| 4,753,245 A | 6/1988 | Gedeon | |
| 4,756,670 A | 7/1988 | Arai | 417/43 |
| 4,757,453 A | 7/1988 | Nasiff | 364/415 |
| 4,781,184 A | 11/1988 | Fife | 128/205.12 |
| 4,793,362 A | 12/1988 | Tedner | |
| 4,796,182 A | 1/1989 | Duboff | 364/413.29 |
| 4,796,639 A | 1/1989 | Snow et al. | 600/532 |
| 4,803,625 A | 2/1989 | Fu et al. | 364/413.03 |
| 4,807,169 A | 2/1989 | Overbeck | 364/715.01 |
| 4,823,808 A | 4/1989 | Clegg et al. | 128/773 |
| 4,850,371 A | 7/1989 | Broadhurst et al. | 600/532 |
| 4,853,854 A | 8/1989 | Behar et al. | 364/413.01 |
| 4,855,942 A | 8/1989 | Bianco | 364/561 |
| 4,855,945 A | 8/1989 | Sakai | 364/709.02 |
| 4,856,531 A | 8/1989 | Merilainen | 600/532 |
| 4,880,014 A | 11/1989 | Zarowitz et al. | |
| 4,891,756 A | 1/1990 | Williams, III | 364/413.29 |
| 4,894,793 A | 1/1990 | Ikemoto et al. | 364/709.03 |
| 4,895,163 A | 1/1990 | Libke et al. | |
| 4,909,259 A | 3/1990 | Tehrani | 600/531 |
| 4,911,175 A | 3/1990 | Shizgal | |
| 4,911,256 A | 3/1990 | Attikiouzel | 177/25.16 |
| 4,914,959 A | 4/1990 | Mylvaganam et al. | 73/861.28 |
| 4,917,108 A | 4/1990 | Mault | |
| 4,924,389 A | 5/1990 | Gerbaulet et al. | 364/413.29 |
| 4,947,862 A | 8/1990 | Kelly | |
| 4,951,197 A | 8/1990 | Mellinger | 364/413.2 |
| 4,954,954 A | 9/1990 | Madsen et al. | 364/413.29 |
| 4,955,946 A | 9/1990 | Mount et al. | 600/532 |
| 4,965,553 A | 10/1990 | DelBiondo, II et al. | 340/573 |
| 4,966,155 A | 10/1990 | Jackson | |
| 4,986,268 A | 1/1991 | Tehrani | 128/204 |
| 4,998,018 A | 3/1991 | Kurahashi et al. | 250/343 |
| 5,007,429 A | 4/1991 | Treatch et al. | |
| 5,012,411 A | 4/1991 | Policastro et al. | 364/413.06 |
| 5,019,974 A | 5/1991 | Beckers | 364/413.02 |
| 5,022,406 A | 6/1991 | Tomlinson | |
| 5,033,561 A | 7/1991 | Hettinger | 177/25.16 |
| 5,038,773 A | 8/1991 | Norlien et al. | 128/205.23 |
| 5,038,792 A | 8/1991 | Mault | |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | |
| 5,060,656 A | 10/1991 | Howard | |
| 5,063,937 A | 11/1991 | Ezenwa et al. | |
| 5,068,536 A | 11/1991 | Rosenthal | 250/341 |
| 5,069,220 A | 12/1991 | Casparie et al. | |
| 5,072,737 A | 12/1991 | Goulding | |
| 5,077,476 A | 12/1991 | Rosenthal | 250/341 |
| 5,081,871 A | 1/1992 | Glaser | 73/863.23 |
| 5,086,781 A | 2/1992 | Bookspan | |
| 5,095,900 A | 3/1992 | Fertig et al. | 128/207.14 |
| 5,095,913 A | 3/1992 | Yelderman et al. | |
| 5,117,674 A | 6/1992 | Howard | 73/31.07 |
| 5,119,825 A | 6/1992 | Huhn | 600/529 |
| 5,178,155 A | 1/1993 | Mault | |
| 5,179,958 A | 1/1993 | Mault | |
| 5,203,344 A | 4/1993 | Scheltinga et al. | |
| 5,214,966 A | 6/1993 | Delsing | 73/861.28 |
| 5,233,520 A | 8/1993 | Kretsch et al. | 364/413.29 |
| 5,233,996 A | 8/1993 | Coleman et al. | 600/529 |
| 5,263,491 A | 11/1993 | Thornton | |
| 5,280,429 A | 1/1994 | Withers | 364/413.15 |
| 5,282,473 A | 2/1994 | Braig et al. | 600/532 |

| | | | | | | |
|---|---|---|---|---|---|---|
| 5,282,840 A | 2/1994 | Hudrlik ............... 607/28 | | 5,908,301 A | 6/1999 | Lutz ............... 434/236 |
| 5,285,794 A | 2/1994 | Lynch | | 5,910,107 A | 6/1999 | Iliff ............... 600/300 |
| 5,293,875 A | 3/1994 | Stone | | 5,913,310 A * | 6/1999 | Brown ............... 600/300 |
| 5,299,579 A | 4/1994 | Gedeon et al. ............... 600/532 | | 5,918,603 A | 7/1999 | Brown ............... 128/897 |
| 5,303,712 A | 4/1994 | Van Duren ............... 600/529 | | 5,922,610 A | 7/1999 | Alving et al. ............... 436/116 |
| 5,307,263 A | 4/1994 | Brown ............... 364/413.09 | | 5,932,812 A | 8/1999 | Delsing ............... 73/861.02 |
| 5,309,921 A | 5/1994 | Kisner et al. ............... 600/532 | | 5,933,136 A | 8/1999 | Brown ............... 345/327 |
| 5,326,973 A | 7/1994 | Eckerbom et al. ............... 250/343 | | 5,941,825 A | 8/1999 | Lang et al. ............... 600/449 |
| 5,335,667 A | 8/1994 | Cha et al. | | 5,951,300 A | 9/1999 | Brown ............... 434/236 |
| 5,355,879 A | 10/1994 | Brain | | 5,957,858 A | 9/1999 | Micheels et al. ............... 600/532 |
| 5,357,972 A | 10/1994 | Norlien | | 5,961,451 A * | 10/1999 | Reber et al. ............... 600/322 |
| 5,363,857 A | 11/1994 | Howard ............... 600/531 | | 5,974,124 A | 10/1999 | Schlueter, Jr. et al. .. 379/106.02 |
| 5,372,141 A | 12/1994 | Gallup et al. | | 5,989,188 A | 11/1999 | Birkhoelzer et al. ............... 600/300 |
| 5,381,796 A * | 1/1995 | Pompei ............... 600/549 | | 5,997,476 A | 12/1999 | Brown ............... 600/300 |
| 5,387,164 A | 2/1995 | Brown, Jr. ............... 482/9 | | 6,010,459 A | 1/2000 | Silkoff et al. ............... 600/532 |
| 5,388,043 A | 2/1995 | Hettinger ............... 364/413.29 | | 6,013,007 A | 1/2000 | Root et al. ............... 482/8 |
| 5,398,688 A | 3/1995 | Laniado | | 6,014,578 A | 1/2000 | Minoz ............... 600/350 |
| 5,398,695 A | 3/1995 | Anderson et al. ............... 600/532 | | 6,015,389 A | 1/2000 | Brown ............... 600/533 |
| 5,402,796 A | 4/1995 | Packer et al. | | 6,024,281 A | 2/2000 | Shepley ............... 235/375 |
| 5,412,560 A | 5/1995 | Dennison ............... 364/413.01 | | 6,024,699 A | 2/2000 | Surwit et al. ............... 600/300 |
| 5,412,564 A | 5/1995 | Ecer ............... 364/413.29 | | 6,030,342 A | 2/2000 | Amano et al. ............... 600/301 |
| 5,415,176 A | 5/1995 | Sato et al. | | 6,032,676 A | 3/2000 | Moore ............... 128/898 |
| 5,419,326 A | 5/1995 | Harnoncourt | | 6,040,531 A | 3/2000 | Miller-Kovach et al. 177/25.16 |
| 5,421,344 A | 6/1995 | Popp | | 6,042,383 A | 3/2000 | Herron ............... 434/238 |
| 5,425,374 A | 6/1995 | Ueda et al. ............... 600/532 | | 6,044,843 A | 4/2000 | O'Neil et al. ............... 128/204.23 |
| 5,449,000 A | 9/1995 | Libke et al. | | 6,045,513 A | 4/2000 | Stone et al. ............... 600/508 |
| 5,450,193 A | 9/1995 | Carlsen et al. ............... 356/301 | | 6,077,193 A | 6/2000 | Buhler et al. ............... 482/8 |
| 5,454,721 A | 10/1995 | Kuch ............... 434/127 | | 6,083,006 A | 7/2000 | Coffman ............... 434/127 |
| 5,468,961 A | 11/1995 | Gradon et al. ............... 250/345 | | 6,095,949 A | 8/2000 | Arai ............... 482/4 |
| 5,485,402 A | 1/1996 | Smith et al. ............... 364/566 | | 6,095,985 A | 8/2000 | Raymond et al. ............... 600/513 |
| 5,503,151 A | 4/1996 | Harnoncourt et al. | | 6,101,478 A | 8/2000 | Brown ............... 705/2 |
| 5,542,420 A | 8/1996 | Goldman et al. | | 6,122,536 A | 9/2000 | Sun et al. ............... 600/341 |
| 5,570,697 A | 11/1996 | Walker et al. ............... 128/719 | | 6,135,950 A | 10/2000 | Adams ............... 600/300 |
| 5,579,782 A | 12/1996 | Masuo | | 6,135,951 A | 10/2000 | Richardson et al. ............... 600/300 |
| 5,611,351 A | 3/1997 | Sato et al. | | 6,309,342 B1 * | 10/2001 | Blazey et al. ............... 600/301 |
| 5,615,689 A | 4/1997 | Kotler | | 6,396,416 B1 * | 5/2002 | Kuusela et al. ............... 340/870.28 |
| 5,632,281 A | 5/1997 | Rayburn | | | | |
| 5,645,071 A | 7/1997 | Harnoncourt et al. ............... 128/719 | | | | |
| 5,647,370 A | 7/1997 | Harnoncourt | | | | |
| 5,673,691 A | 10/1997 | Abrams et al. | | | FOREIGN PATENT DOCUMENTS | |
| 5,676,132 A | 10/1997 | Tillotson et al. ............... 128/204.23 | | EP | 0459647 A2 * 12/1991 | |
| 5,678,562 A | 10/1997 | Sellers | | EP | 0 712 638 12/1995 | |
| 5,678,571 A | 10/1997 | Brown ............... 128/898 | | EP | 1013221 A1 * 6/2000 | |
| 5,691,927 A | 11/1997 | Gump ............... 364/709.01 | | GB | 2323292 9/1998 | |
| 5,704,350 A | 1/1998 | Williams, III | | WO | WO 96/40340 12/1996 | |
| 5,705,735 A | 1/1998 | Acorn ............... 73/23.3 | | WO | 99/60925 * 5/1999 | |
| 5,720,296 A | 2/1998 | Cha ............... 128/734 | | | | |
| 5,729,479 A | 3/1998 | Golan ............... 364/709.2 | | | OTHER PUBLICATIONS | |
| 5,746,214 A | 5/1998 | Brown et al. | | | | |
| 5,754,288 A | 5/1998 | Yamamoto et al. ............... 356/301 | | British Journal Of Anaesthesia, vol. 49, 1977 London (GB) pp. 575–587, J. A. Bushman et al. "Closed Circuit Anaesthesia." | | |
| 5,788,643 A | 8/1998 | Feldman ............... 600/506 | | | | |
| 5,789,660 A | 8/1998 | Kofoed et al. ............... 73/232 | | | | |
| 5,796,009 A | 8/1998 | Delsing ............... 73/861.28 | | | | |
| 5,796,640 A | 8/1998 | Sugarman et al. ............... 364/709.02 | | IEEE Transactions on Biomedical Engineering, vol. 35, No. 9, Sep. 1988, pp. 653–659, Capek et al., "Noninvasive Measurement of Cardia Output Using Partial CO2 ReBreathing." | | |
| 5,800,360 A | 9/1998 | Kisner et al. ............... 600/532 | | | | |
| 5,810,722 A | 9/1998 | Heikkila ............... 600/300 | | | | |
| 5,816,246 A | 10/1998 | Mirza | | | | |
| 5,817,031 A | 10/1998 | Masuo et al. ............... 600/547 | | | | |
| 5,819,735 A | 10/1998 | Mansfield et al. ............... 128/630 | | Clinics in Chest Medicine (Review), vol. 10, 1989, pp. 255–264, Heigenhauser et al., "Measurement if Cardiac Output by Carbon Dioxide Rebreathing Methods." | | |
| 5,822,715 A | 10/1998 | Worthington et al. ............... 702/19 | | | | |
| 5,827,179 A * | 10/1998 | Lichter et al. ............... 600/300 | | | | |
| 5,831,175 A | 11/1998 | Fletcher-Haynes ............... 73/861.28 | | | | |
| 5,832,448 A | 11/1998 | Brown ............... 705/2 | | Determination Of Nitric Oxide Levels By Fluorescence Spectroscopy, Gabor G. and Allon, N. In Biochemical, Pharmacological, and Clinical Aspects of Nitric Oxide, edited by B. A. Weissman et al, Plenum Press, New York, 1995, pp. 57. | | |
| 5,834,626 A | 11/1998 | DeCastro et al. ............... 73/23.3 | | | | |
| 5,836,300 A | 11/1998 | Mault ............... 128/204.23 | | | | |
| 5,836,312 A | 11/1998 | Moore ............... 128/897 | | | | |
| 5,876,351 A * | 3/1999 | Rohde ............... 600/300 | | | | |
| 5,890,128 A | 3/1999 | Diaz et al. ............... 705/2 | | | | |
| 5,897,493 A | 4/1999 | Brown ............... 600/300 | | | | |
| 5,899,855 A | 5/1999 | Brown ............... 600/300 | | * cited by examiner | | |
| 5,902,234 A | 5/1999 | Webb ............... 600/300 | | | | |

PHYSIOLOGICAL MONITOR AND ASSOCIATED COMPUTATION, DISPLAY AND COMMUNICATION UNIT

REFERENCE TO RELATED APPLICATIONS

This application claims priority from U.S. provisional application Serial Nos. 60/155,851, filed Sep. 24, 1999; 60/158,553, filed Oct. 8, 1999; 60/158,556, filed Oct. 8, 1999; 60/158,554, filed Oct. 8, 1999; 60/159,285, filed Oct. 13 1999; 60/165,166, filed Nov. 12, 1999; 60/165,988, filed Nov. 17, 1999; 60/167,276, filed Nov. 24, 1999; 60/177,011, filed Jan. 19, 2000; 60/177,016, filed Jan. 19, 2000; 60/177,009, filed Jan. 19, 2000; 60/178,979, filed Jan. 28, 2000; 60/179,882, filed Feb. 2, 2000; 60/194,126, filed Apr. 3, 2000; 60/201,902, filed May 4, 2000; 60/195,779, filed Apr. 10, 2000; 60/205,709, filed May 19, 2000; 60/206,905, filed May 25, 2000; 60/207,089, filed May 25, 2000; 60/207,051, filed May 25, 2000; 60/209,921, filed Jun. 7, 2000; 60/212,319, filed Jun. 16, 2000; 60/219,069, filed Jul. 18, 2000; 60/219,070, filed Jul. 18, 2000; 60/224,651, filed Aug. 11, 2000; 60/225,101, filed Aug. 14, 2000; 60/225,454, filed Aug. 15, 2000; 60/228,388, filed Aug. 28, 2000; 60/234,154; filed Sept. 21, 2000; and 60/234,866, filed Sep. 22, 2000, the entire contents of all of which are incorporated herein by reference.

FIELD OF THE INVENTION

The present invention relates generally to physiological monitors and, more specifically, to physiological monitors that connect with and/or communicate with a hand-held computing device such as a personal digital assistant (PDA).

BACKGROUND OF THE INVENTION

Portable electronic computing devices have become increasingly common. These devices include personal digital assistants (PDAs) such as organizers using the PALM® operating system and organizers using Windows® CE based operating systems. These devices also include other portable electronic devices that include a computing capability such as mobile telephones, electronic books, laptop and hand-held computers, some types of pagers, hand-held game platforms such as the Nintendo® Gameboy® and other devices.

The prevalence of PDAs, and their broad acceptance by many of types of users, provides an opportunity to offer accessories to PDAs which may be used by this large installed base. Also, the PDAs can act as a general purpose computing device. In this capacity, the PDA may be interconnected with a variety of accessories and provide the necessary computing, control and display functions for the accessory, thereby reducing the cost of the accessory as compared to a stand along device. As an example, digital camera modules are available which interconnect with the PDAs of several types. When the camera module is interconnected with PDA, the PDA's buttons and display serve to control and communicate the camera functions, thereby eliminating the need for controls or a display on the camera module itself. Also, the PDA's internal computing capability is used, thereby avoiding the necessity of on-board computing capability in the camera module. Consequently, the camera module is both smaller and less expensive than a stand-alone camera of similar capability.

Physiological monitors of various types are used in the health and medical fields to monitor various physiological parameters of human patients. These physiological monitors allow health and medical professionals, as well as individual users, to accurately determine the current status of particular physiological parameters and monitor those parameters over a period of time. This information is extremely helpful in health and fitness management and medical treatment. Traditionally, physiological monitors have been very expensive, and their use has therefore been primarily limited to medical facilities. As the cost of electronic equipment has fallen, lower cost physiological monitors have been used in the home.

An example of a health related physiological monitor is the indirect calorimeter disclosed in co-pending U.S. patent application Ser. No. 09/630,398 to Mault et al,, which is incorporated herein in its entirety by reference. The indirect calorimeter allows a patient to determine their current metabolic rate by breathing through the calorimeter for a period of time. As explained in the application, this metabolic rate information is beneficial in weight and health management. Other types of physiological monitors include EKG monitors, electronic heart sound monitors, exercise monitors such as pedometers, body fat measurement devices, heart rate monitors, body temperature monitors, spirometers, blood pressure monitors, blood oxygenation monitors, and blood glucose monitors. Typically, physiological monitors are stand-alone devices including their own controls, displays, and, if necessary, computing capability. Consequently, these physiological monitors tend to be expensive and potentially bulky.

Current physiological monitors typically do not communicate with one another or with any type of central computing device. If a health care professional or a patient measures, or monitors over time, numerous physiological parameters, it is typically necessary to record the output from each individual monitor and then to manually transfer the data to the patient's medical record. This is laborious and introduces potential for error in recording and transferring the data. The process can be especially laborious where physiological parameters are monitored over long periods of time. For example, it is necessary for some diabetics to test their blood glucose level numerous times each day. Preferably, this data is recorded so that trends may be determined and shared with a physician or other health professional. However, a typical patient will get tired of constantly recording blood sugar levels and may therefore do a poor job.

SUMMARY OF THE PRESENT INVENTION

The present invention includes a variety of physiological monitor modules designed to interface with computing devices such as PDAs. In some embodiments, this combination allows the PDA to take the place of some of the costly electronic controls, displays, and processing circuitry normally embodied in a physiological monitor. Instead, the PDA provides these capabilities. Also, the PDA preferably stores testing data from one or more physiological monitor modules to allow the use of data in health and fitness tracking as well as in a variety of software applications. In another embodiment of the present invention, the physiological monitor modules include storage means such as memory for storing data from one or more sensors. Either during or after the test, the data from the storage means is transferred to the PDA for processing, display, and storage. In another embodiment of the present invention, the PDA is of the type including an accessory slot for accepting modules such as memory modules. In this embodiment, the physiological monitor module also includes an accessory slot for accepting a memory module. Memory modules are then used to transfer data between the physiological monitor and the PDA.

DETAILED DESCRIPTION OF THE PREFERRED EMBODIMENTS

General

Figure 1A:
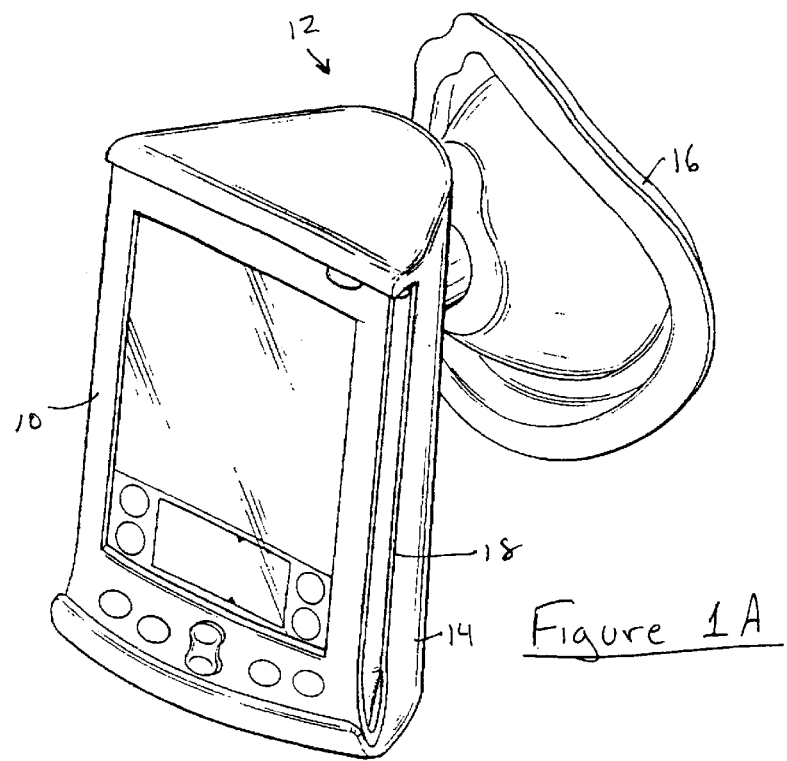
FIG. 1A is a perspective view of a calorimeter module according to the present invention docked with a PDA.

This invention relates to a physiological monitor for use in measuring a health characteristic of a user, such as metabolism, weight, body fat percentage, heart rate, EKG, blood pressure, blood oxygenation, body temperature or the like, and an associated computing device which acts to receive, record, process, compute, display and/or transmit signals from the monitor. The computing device may take any form, including portable computers such as personal digital assistances (PDAs) as well as non-portable computers. The portable computer category includes all portable devices with onboard computing capability, such as cellular telephones, electronic books, pagers, watches, and organizers. Also included are currently available, as well as yet to be developed, wearable computing devices such as may take the form of jewelry, buttons, and eyeglasses. The PDA need not be a unitary device, but instead the components could be distributed. As one example, the display could be incorporated in eyeglasses while the remainder is incorporated into a wristwatch. For ease of reference, the present application will refer primarily to PDAs, though all other computing devices may be used as well. The term "general purpose personnel digital assistant" will also be used herein. This refers to a PDA capable of running a variety of software that may be loaded into memory. This category excludes dedicated devices and non-programmable devices.

According to a first preferred embodiment of the present invention, the physiological monitor is a module designed to interconnect with a PDA, such as by docking with the PDA. The PDA is preferably of the type adapted to receive a variety of plug-in modules, each of which may provide the PDA with a particular application program. Alternatively, the application software may be stored in the memory of the PDA, or in other ways. The physiological monitor modules used with the present invention also incorporate connections to the sensors forming part of the physiological monitor, and may include electronics that act as an interface between the sensors of the physiological monitor and the PDA. In this embodiment, when the PDA and monitor module are docked, they form an integral unit. The module may insert into an accessory slot in the PDA, or grip its housing, or interconnect in any other way.

Preferably, when the monitor module is docked with the PDA, the PDA recognizes the module and loads the software either from its own memory or from the module. As known to those of skill in the art, recognition of the module by the PDA may take several forms. The module may have a code either temporarily or permanently stored in its memory. Plugging the module into the PDA causes the code to be transferred to the PDA where the code may be interpreted to identify the module and/or the user. As another alternative, the PDA may include bar code scanning capability and the module may include a bar code that may be scanned prior to inserting the module. When the monitor module is not in use, the PDA may be removed and used for alternative purposes, possibly with other modules.

During use of the monitor module, the PDA may display instructions for use. If the PDA and module combination includes voice generation capability, either as part of the PDA itself, as part of the module itself, or as an additional accessory, voice commands may be generated to instruct the user on proper use of the monitor module and/or to provide feedback and results. If voice recording or recognition is available in the combination, this capability may be used to control the module and/or annotate results. Voice recognition and generation capability may be provided as an additional accessory for the PDA or monitor module or the monitor module may include these capabilities. Voice recognition modules are more completely described in co-pending provisional patent application Ser. No. 60/212,319, which is incorporated herein in its entirety.

The physiological monitor module may dispense with controls, memory, processing, and/or a display, instead relying on the PDA to provide these functions. In this case, it may be necessary to first dock the PDA with the monitor module in order to use the monitor. Alternatively, the physiological monitor may be operational without being interconnected or in communication with a PDA. Instead, the physiological monitor measures one or more physiological parameters and stores the resulting data to memory. Optionally, the monitor may have onboard data processing and/or display. At a later time, the physiological monitor may be interconnected with, or otherwise placed in communication with, a PDA so that data may be transferred from the monitor to the PDA. The PDA may enable additional functionality or provide processing and display of physiological data. With any of the above embodiments, wired or wireless communication may substitute for the physical docking of the PDA with the monitor module. Wireless communication may take any form including radio frequency communication such as the Bluetooth® protocol, infrared communication, and others.

As another alternative, data may be transferred between a physiological monitor and a PDA using memory modules. In this embodiment, the PDA and monitor both include accessory slots into which a memory module may be inserted. During or after use of the monitor, the memory module is inserted into the accessory slot and data is stored to the module. The module may then be inserted into the accessory slot of the PDA for download of data, processing, and display. The memory module may serve other purposes such as including onboard processing, application software, or calibration or software updates. The module may also include data about a particular patient or group of patients. The PDA and/or monitor may recognize the module using stored codes, bar code scanning, or other approaches. Alternatively, either the monitor or the PDA may receive a module in addition to docking with or communicating with each other.

In one preferred embodiment of the present invention, a physiological monitor module takes the form factor typical of a memory module, such that the monitor module may be inserted into an accessory slot in a PDA or other computing device, either directly or via an adapter. In this embodiment, the monitor module may be worn or placed on a user's body as necessary to measure a particular physiological parameter. Accessory clips may be used to interconnect the monitor module with the person's body or clothing. After measurements are taken, the monitor module is removed from the person or from the accessory clip and inserted into the PDA for download and processing of data. Alternatively, the monitor module may include it's own small display and/or controls. As a further alternative, the monitor module may include on-board wireless communication capability so that the module may continuously or intermittently communicate with a PDA or other computing device. The monitor module may be formed as one or more computer chips with the necessary sensors, memory, and communication hardware forming part of the chip. For example, a single chip may include all of the necessary hardware to function as a monitor module, and be shaped so as to fit into an accessory slot in a PDA, either directly or via an adapter. Wireless communication circuitry may be formed right on the chip, along with memory, and/or sensing hardware.

As will be clear to those of skill in the art, almost any type of physiological monitor may be incorporated into the present invention. Examples of physiological monitors, which will be described in more detail below, include a calorimeter module for measuring metabolic rate, a spirometer module for measure breath flow and volume, a pedometer module for measuring motion, a heart rate, an EKG/heart sound module, or a pulse oximeter for measuring cardiac-related parameters, a body fat module, a blood pressure module, a body temperature module, a blood glucose module, an ultrasonic sensor for measuring respiration, pregnancy-related factors, bone density, or posture, a food or body weight module, and others. Each of the above described embodiments and alternatives, as well as others that will be described, apply to each of the physiological monitors described hereinbelow.

Preferably, the various embodiments of the present invention are used as part of a weight or health management system, aspects of which are described in co-pending provisional patent application Ser. Nos. 60/158,553; 60/167,276; 60/177,016; 60/194,126; 60/209,921; 60/201,902; 60/207,089; and 60/207,051. As part of the system, caloric intake, resting metabolism, and activity-based metabolic expenditures are tracked. For example, a PDA, which is normally carried by a user, includes software for logging calorie consumption and activities. The physiological monitors according to the various embodiments of the present invention preferably integrate with such a health management system. For example, data from a calorimeter module may be used to determine baseline caloric expenditure. This is a very important factor in dietary management. The PDA may periodically prompt the user to measure their resting metabolic rate using the calorimeter module. The data from the measurement is then automatically entered into the health management program. The software may also allow the user to postpone the measurement until a more appropriate time.

Preferably, the PDA includes software which prompts or reminds a user to make use of the various physiological monitor modules as part of an overall health management system. For example, the PDA may prompt a user, on a weekly basis, to use a body weight scale module or to transfer data already stored in the scale. Alternative, the PDA may periodically wirelessly query various physiological monitors within its wireless transmission range in order to transfer data and to determine when each module was last used.

The health management software may include the ability to set up a variety of fitness plans and to track adherence to the plans. For example, a particular user may specify that they will walk or run a certain number of times and for a certain distance each week. The software may then prompt the user to remind them that, according to the schedule, they should run or walk a certain distance on a particular day. The person uses a pedometer module, either on its own or mated with a PDA, to measure their performance during a run or walk. This data is transferred into the PDA and used by the software to determine how the person's performance compares to their goals. As part of the health or fitness management program, it may be preferable to track other factors such as blood pressure, heart rate, or blood glucose. The PDA may also prompt the user to measure these parameters at appropriate times. The user may then insert the appropriate module into the PDA, perform the appropriate test, and have the data automatically transferred into the program.

As a further aspect of the health management software, it is preferred that the PDA communicates with remote computing devices and/or health professionals. For example, the PDA may include wireless communication capability such that it may wirelessly communicate, via the Internet or other means, with a remote server. The remote server may store and analyze the data received from the PDA and provide feedback based on the information. The information from the PDA may also be reviewed by a health professional or health management advisor so that feedback may be given. The feedback may be communicated back to the PDA or communicated to the user in other ways. The health management software may reside in the PDA's memory, in a plug-in module, or in a memory of a monitor module.

Calorimeter Module

Figure 1B:
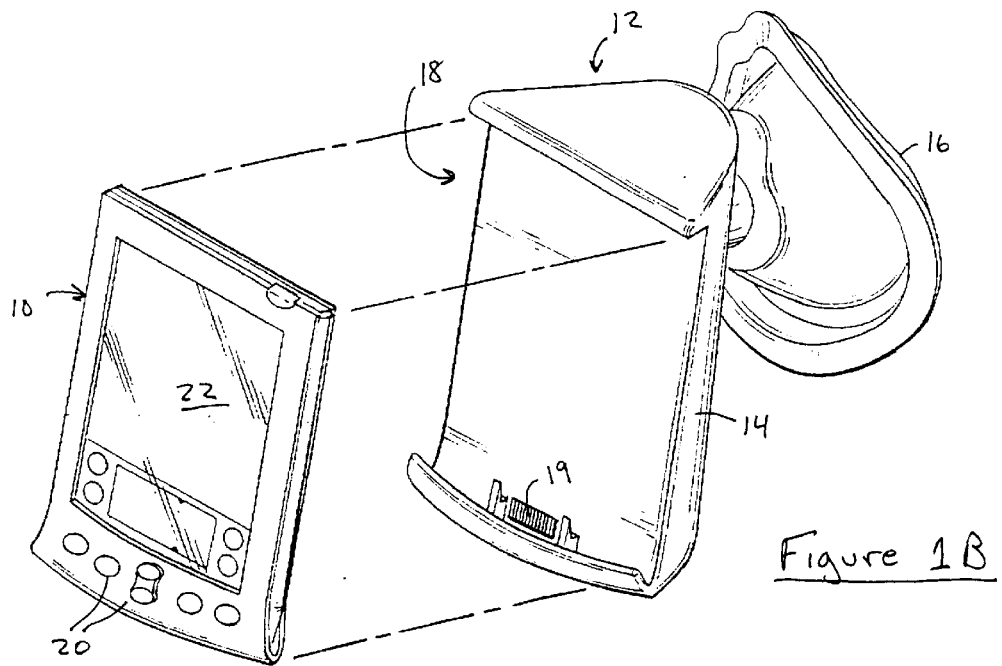
FIG. 1B is a perspective view of a calorimeter module and PDA of FIG. 1A with the PDA removed from the docking interface.

Referring to FIGS. 1A and 1B, a calorimeter module that interconnects with a PDA 10 is generally shown at 12. The calorimeter module 12 is constructed in accordance with the disclosure of co-pending U.S. patent application Ser. No. 09/630,398 to Mault et al. (incorporated herein in its entirety by reference), and may be best understood by reference thereto. In one embodiment, the calorimeter module 12 includes a body 14 with a respiratory connector 16 extending from the side. The body 14 contains an internal flow path, a bi-directional flow meter, and one or more gas concentration sensors. In use, a patient breathes through the respiratory connector 16 for a period of time and the calorimeter module 12 measures parameters such as inhalation volume, exhalation volume and the concentration of oxygen in the exhalation. These measurements may be used to determine metabolic rate. Unlike the calorimeter described in the co-pending application, the calorimeter module 12 for use with the present invention preferably does not include its own controls, display, or onboard CPU. Instead, the module 12 includes a docking interface 18 for interconnection with the PDA 10. In the embodiment illustrated in FIG. 1, the docking interface 18 is a C-shaped opening that grips the upper and lower ends of the PDA 10. In the illustrated embodiment, the PDA 10 is one of the PalmPilot® family of PDAs, which include electrical contacts on the lower back edge of the outer case. As best shown in FIG. 1B, the docking interface 18 has corresponding electrical contacts 19 that mate with the electrical contacts on the back of the PDA when the PDA is docked in the docking interface 18.

In order to use the calorimeter module 12, the user first docks the PDA 10 into the docking interface 18. The buttons 20 on the PDA are then used to control the operation of the calorimeter module 12. The display 22 of the PDA is used to communicate information from the module 12 to the user. The internal CPU in the PDA 10 is used to provide all or part of the computational analysis necessary for the calorimeter module. The PDA's display 22 may present instructions on how to perform the test as well as presenting test results, or any error messages. If the PDA includes voice recognition, voice generation, or recording capabilities, these may be used as well. Following the test, the user may remove the PDA 10 from the docking interface 18 so that the PDA may be used with other physiological monitors or as a PDA. The information received by the PDA during the calorimeter test is stored in the PDA. At a later time, the user may dock the PDA with another computer for downloading the information to the computer or for interconnection with remote commuters, such as via the Internet. The PDA may also directly communicate with remote computers, such as by using a wired or wireless modem. The calorimeter module may include memory that stores application software for the PDA or the application software may be resident in the PDA. Preferably, when the PDA is docked in the docking interface, the PDA recognizes the module, as previously described, and loads the application software, either from the module or from the PDA's memory. The software, if stored in the module, may be permanently stored or may be updatable in various ways. The module may include capabilities such as voice recognition, voice generation, or recording, as necessary, to supplement the capabilities of the PDA.

As an alternative, the calorimeter module 12 may include its own internal processor and/or control buttons and a display, along with the docking interface 18. With this embodiment, the user may utilize the calorimeter module 12 without a PDA 10 docked in the docking interface 18. Then, at a later time, the PDA may be docked with the calorimeter for transfer of data. Docking of the PDA 10 with the docking interface 18 may also enable additional functionality, such as graphical display of information.

As a further alternative, the calorimeter module may include onboard memory, but lack the processing circuitry of a complete calorimeter. During use, data from the various sensors is stored to the memory, preferably along with time data. After use, the data is transferred to a PDA for processing. This eliminates some parts in the module, reducing its cost, complexity, bulk, and weight. Power consumption and heat generation by the internal circuitry of the calorimeter module may also be reduced. The reduction in heat generation may provide benefits with respect to sensor accuracy.

While it is preferred that the calorimeter module that forms part of the present invention be constructed in accordance with the co-pending Mault et al. application, other calorimeter designs may be used. In each case, the calorimeter functions as a module that interconnects or otherwise communicates with a PDA, either during or after use.

Figure 2:
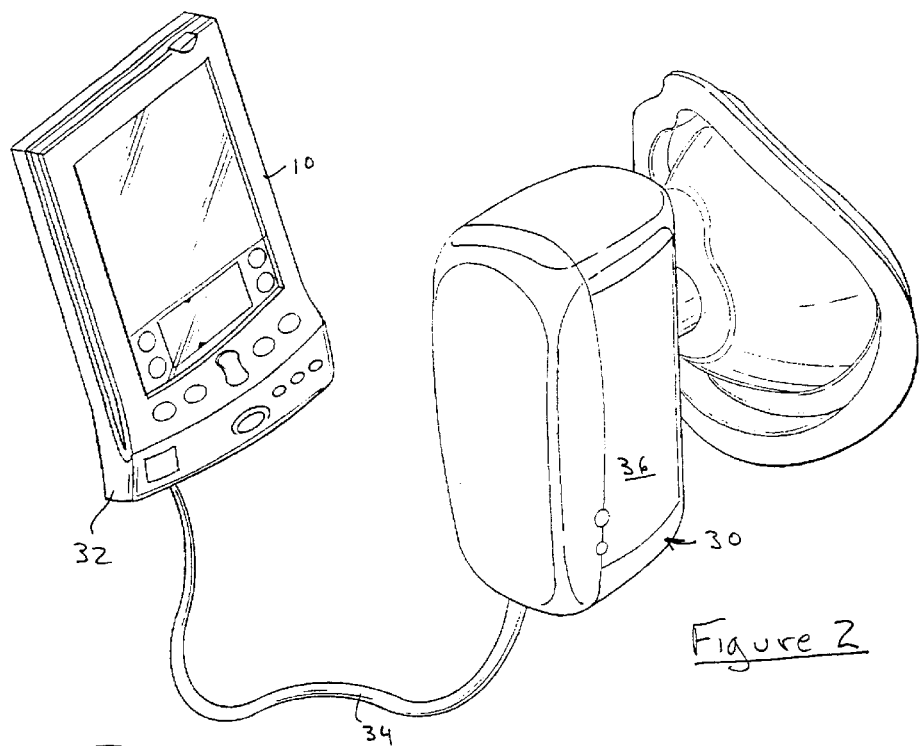
FIG. 2 is a perspective view of a second embodiment of a calorimeter module wherein the docking interface is interconnected with the remainder of the module by a wire.

Referring now to FIG. 2, an alternative embodiment of a calorimeter module 30 for use with a PDA 10 is shown. This embodiment differs from the previous embodiment in that the docking interface 32 is interconnected with the body 36 of the calorimeter module 30 by a wire 34. This allows the PDA 10 in the docking interface 32 to be held in the hand of the user so that it may be viewed during use, or it may be held by another person monitoring the test. Alternatively, the wire 34 may be eliminated by providing wireless communication ability between the calorimeter module 30 and the docking interface 32. Any type of wireless communication may be used. As with the previous embodiment of the calorimeter module, the module 30 may be operational without a PDA, may store data to memory for later processing, or may include controls and/or a display. Alternatively, the calorimeter module may interconnect or communication with a desktop or other computer for use in settings where the larger computer is not a hinderance.

Figure 3:
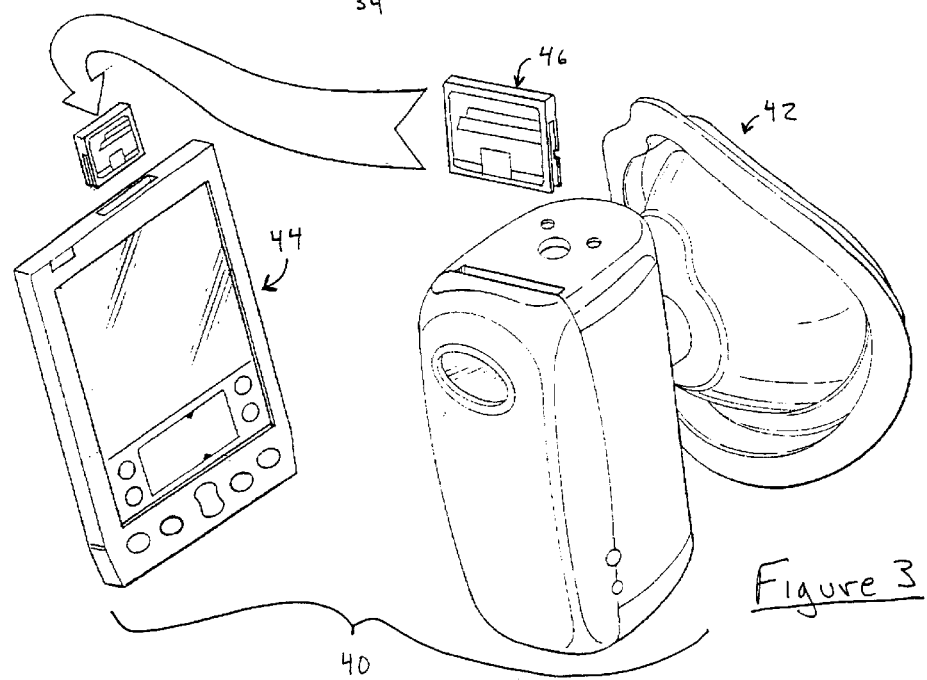
FIG. 3 is a perspective view of a third embodiment of a calorimeter module along with a PDA wherein each utilize memory modules for transfer of data.

Referring now to FIG. 3, an additional embodiment of a calorimeter system is generally shown at 40. The calorimeter system includes a calorimeter 42, a PDA 44, and a memory module 46 used to transfer data between the calorimeter 42 and the PDA 44. As shown, both the calorimeter 42 and the PDA 44 include accessory slots, 48 and 50, respectively, designed to receive the memory module 46. Some currently available PDAs include accessory slots of various types and it is understood that this feature will become more common in the future. The illustrated position, size, and shape of the accessory slots 48 and 50 are for illustration purposes only and it should be understood that other designs may be substituted.

The slots 48 and 50 acts a female connectors and the memory module 46 acts as a male connector. As will be clear to those of skill in the art, there are a variety of memory modules which may be used with this application. Some are typically known as flash memory cards and include CompactFlash, SmartMedia, MultiMediaCard, and MemoryStick™. These memory modules may be non-volatile memory or battery-supported volatile memory and include electrical contacts designed to mate with or abut electrical contacts in the slots 48 and 50. Alternatively, inductive or other wireless interconnects between the memory module 46 and the PDA 44 or calorimeter 42 may be provided. Other memory module types include magnetic memory, optical memory, and solid state memory. The memory module 46 may also include additional capabilities such as on-board processing or storage, or calibration or other data. For example, the module 46 may include application software for the PDA and/or the calorimeter, or may include software updates for either of the devices. Also, the module 46 may provide the PDA and/or calorimeter with speech recognition, voice generation, recording, wireless or wired communication, or other capabilities.

As an alternative, a calorimeter or calorimeter module may be provided with both a PDA docking interface and with an accessory slot so the PDA may be docked with the calorimeter module and a memory module may be inserted into the accessory slot. This would allow application software, calibration updates or other information to be stored on the memory module. As a further alternative, the calorimeter or calorimeter module may be configured to use with a mechanical ventilator or anesthesia equipment, such as by being placed in-line.

Figure 4:
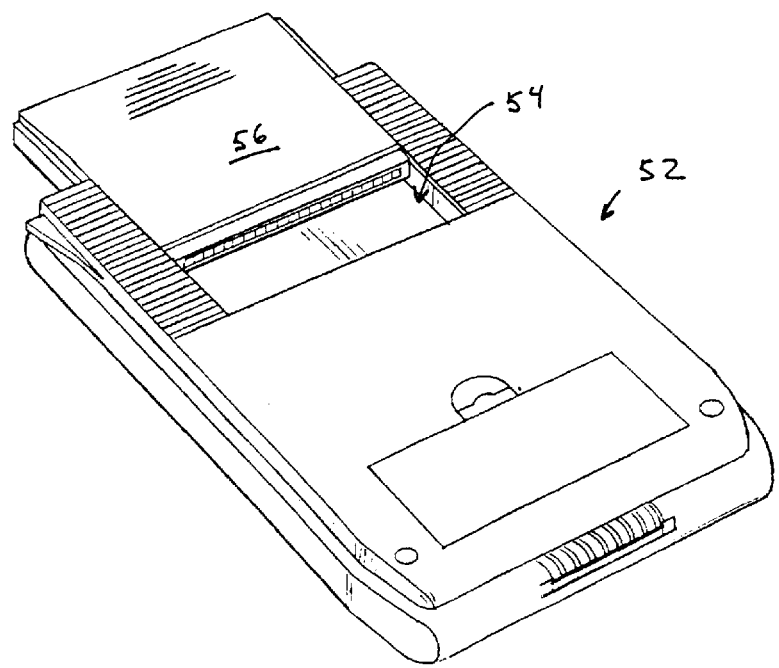
FIG. 4 is a perspective view of the back side of a PDA sold under the brand Handspring Visor®.
Figure 5:
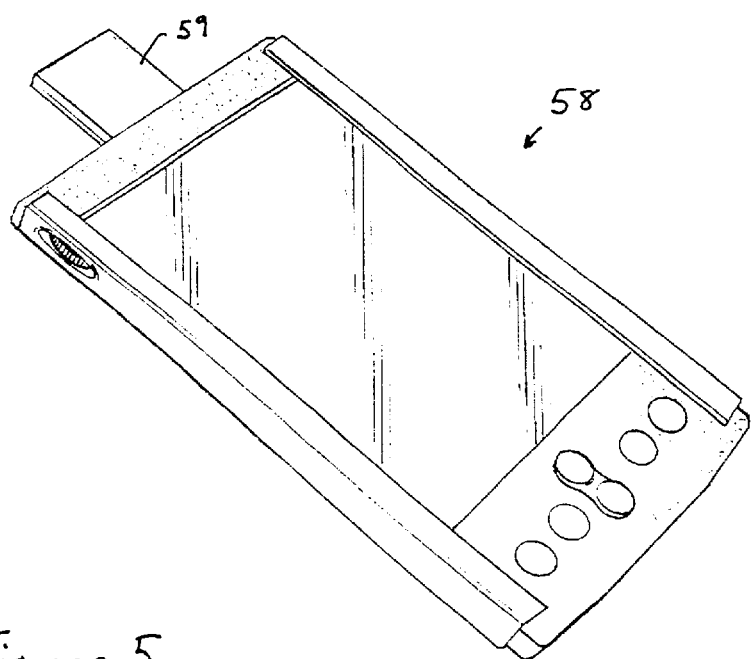
FIG. 5 is a perspective view of a PDA sold by Sony®.

Turning now to FIGS. 4 and 5, other types of PDAs are illustrated. FIG. 4 illustrates a PDA 52 sold under the name Handspring Visor®. The Handspring Visor® includes an accessory slot 54 referred to as the Springboard®. This accessory slot serves two purposes. First, it allows for interconnection with accessories such as memory modules and digital camera modules. Secondly, the slot serves as a mounting means for physical interconnection with the accessory. In FIG. 4, a module 56 is shown being inserted into the Springboard® accessory slot. The module 56 is approximately the same size as the slot so that when it is fully inserted it is flush with the outer case of the PDA. Other larger accessories include a tab that engages with the accessory slot while the overall accessory extends beyond the PDA. As will be clear to those of skill in the art, the docking interface on the calorimeter module in FIGS. 1A and 1B may take a different form such that it is designed to interconnect with an accessory slot of the type used on a Handspring Visor®. This is also true for the calorimeter module of FIG. 2. The Springboard® also may accept memory modules, either directly or using an adaptor, so as to function as shown in FIG. 3.

Referring now to FIG. 5, yet another PDA 58 is shown which includes an accessory slot designed to accept a memory module 59. The PDA 58 illustrated in FIG. 5 is a Sony® PDA which includes an accessory slot designed to accept memory modules of the MemoryStick™ format. As shown, the MemoryStick™ inserts into a slot at the top of the PDA. Contacts on the MemoryStick™ and in the slot allow interconnection and communication between the MemoryStick™ and the PDA. According to the present invention, physiological monitors may also be interconnected with a PDA of the design shown in FIG. 5 by including a docking interface that inserts into the accessory slot to make a physical interconnection and an electrical connection. Also, a wire may interconnect with any of the illustrated PDAs by engaging an accessory slot or by plugging into a communication plug on the PDA. Similar connections may be made with other currently available, as well as yet to be developed PDAs. Alternatively, a module may slide into an accessory slot in any of the designs of PDA and may provide the PDA with wireless communication capability for use with the physiological monitor or other devices.

As will be clear to those of skill in the art, the present invention may be adapted to work with practically any PDA by providing an appropriate docking interface and/or communication system. For example, if a cellular telephone is to serve as the PDA, the docking interface would take the form of a telephone docking station of some type. Other examples will be clear to those of skill in the art.

Spirometer Module

The calorimeter thus far discussed determines metabolic rate by measuring flow rates and component gas concentrations. For some applications, this much information is not necessary. Instead, for some applications it is desirable to determine flow rate or flow volume only. For example, patients with asthma may benefit from periodic lung volume and flow rate measurements. Devices designed to measure these factors are generally known as spirometers. The calorimeter as previously described includes the capability of measuring instantaneous flow rates through a flow tube within the calorimeter. This data may be used to determine various lung capacity and flow rate measurements. Therefore, a simplified calorimeter may be used as a spirometer and interconnect or communicate with a PDA for this purpose. As another alternative, a very simple flow tube with flow measurement capability may be provided as a physiological monitor module for interconnection with a PDA.

Figure 6:
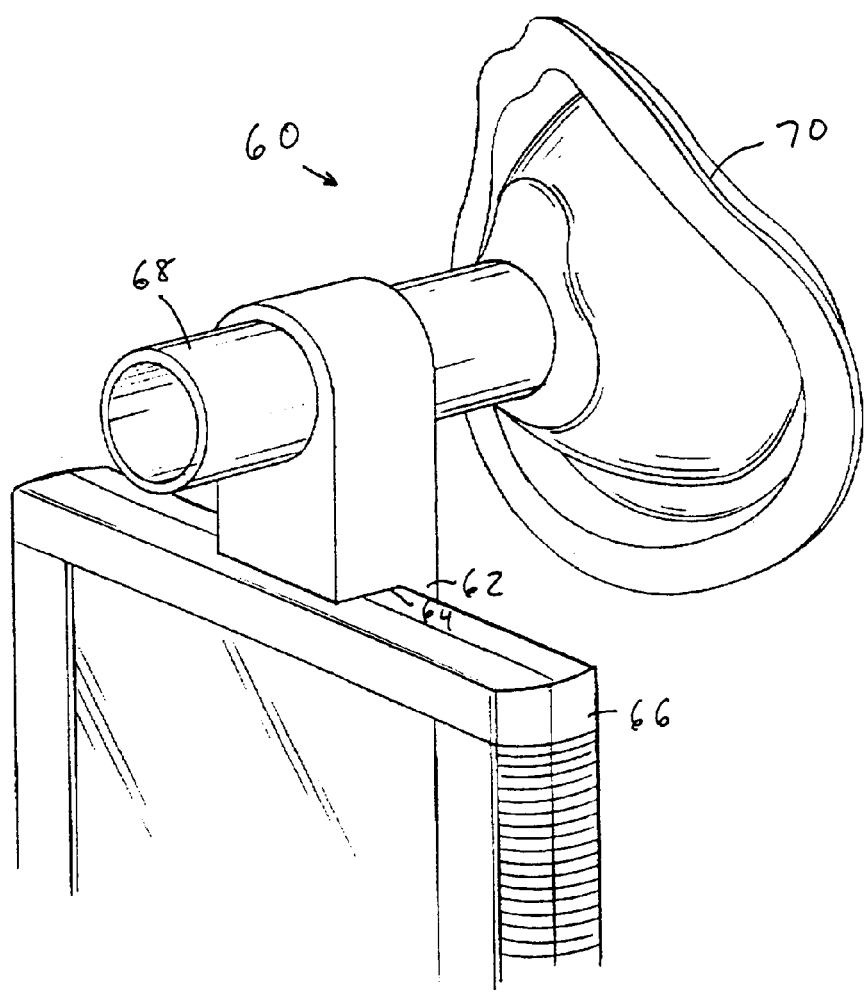
FIG. 6 is a side elevational view of a spirometer module and a PDA.

Referring now to FIG. 6, a simplified spirometer module is shown that includes an attachment flange 62 designed to engage an accessory slot 64 in a PDA 66. As shown, the simplified spirometer module includes a flow tube 68 and a breathing mask 70. The mask serves as a respiratory connector, but other connectors may be used. In order to use the device, the user first inserts the attachment flange 62 into the accessory slot to couple the spirometer module 60 with the PDA 66. Preferably, coupling the two devices causes the PDA 66 to recognize the presence of the spirometer module 60 and to run appropriate software. The PDA may display instructions to the user on how to use this spirometer module. The user then follows the instructions to use the spirometer module to measure the appropriate lung function, such as flow rate or lung volume.

As will be clear to those of skill in the art, the spirometer module 60 may use various types of flow measurement devices including ultrasound-based flow measurement, and pressure-drop-based measurement, small turbines, or other devices. The spirometer module preferably has the coaxial flow geometry and ultrasonic transducer flow sensing of the indirect calorimeter described in co-pending U.S. application Ser. 09/630,398 to Mault et al. According to one preferred embodiment, a stand alone spirometer may include an accessory slot designed to accept memory modules which may then be moved to the PDA. Wireless or wired communication may also be used. Other alternatives, as described for the calorimeter, also apply to the spirometer.

According to one embodiment, the flow profile of a breath (or the average of several breaths) is presented graphically on the display of the PDA, for example in terms of flow rate vs. time from breath onset. The flow profile can be used in respiratory diagnosis. The breath flow profile can be parameterized (for example in terms of peak flow, flow rate changes) or curve fitted, and compared to representative data for normal (healthy) breaths and to breath flow profiles associated with respiratory ailments of various degrees of severity. In particular, this configuration is of great use to people suffering from asthma in tracking the severity of symptoms. Various respiratory parameters may also be determined, such as the forced expiratory volume during the first second (FEV1), forced expiratory flow during other parts of the breath such as FEF 25%–75%, forced vital capacity (FVC), and peak expiratory flow (PEF). Respiratory parameters may be tracked over time, transmitted to a physician over a communications network, transmitted to a computer expert system for diagnosis, stored in a database such as a patient record, correlated with other physiological or environmental parameters, or otherwise characterized. Breath flow profiles and derived respiratory parameters may be used to determine the amount of medication needed by the person using software loaded onto the PDA.

Gas sensors in the flow path are not required for spirometry applications, and hence the spirometer module can be less complex than the indirect calorimeter. However, for some applications, it may be beneficial to provide a gas sensor in the flow path. One example is the detection of nitric oxide (NO), as described in co-pending provisional patent application Ser. No. 60/159,285. Other gas sensors are described in a co-pending provisional patent application entitled "Respiratory Gas Sensors in the Flow Path," filed Aug. 28, 2000 by Mault.

Pedometer Module

Figures 7, 8:
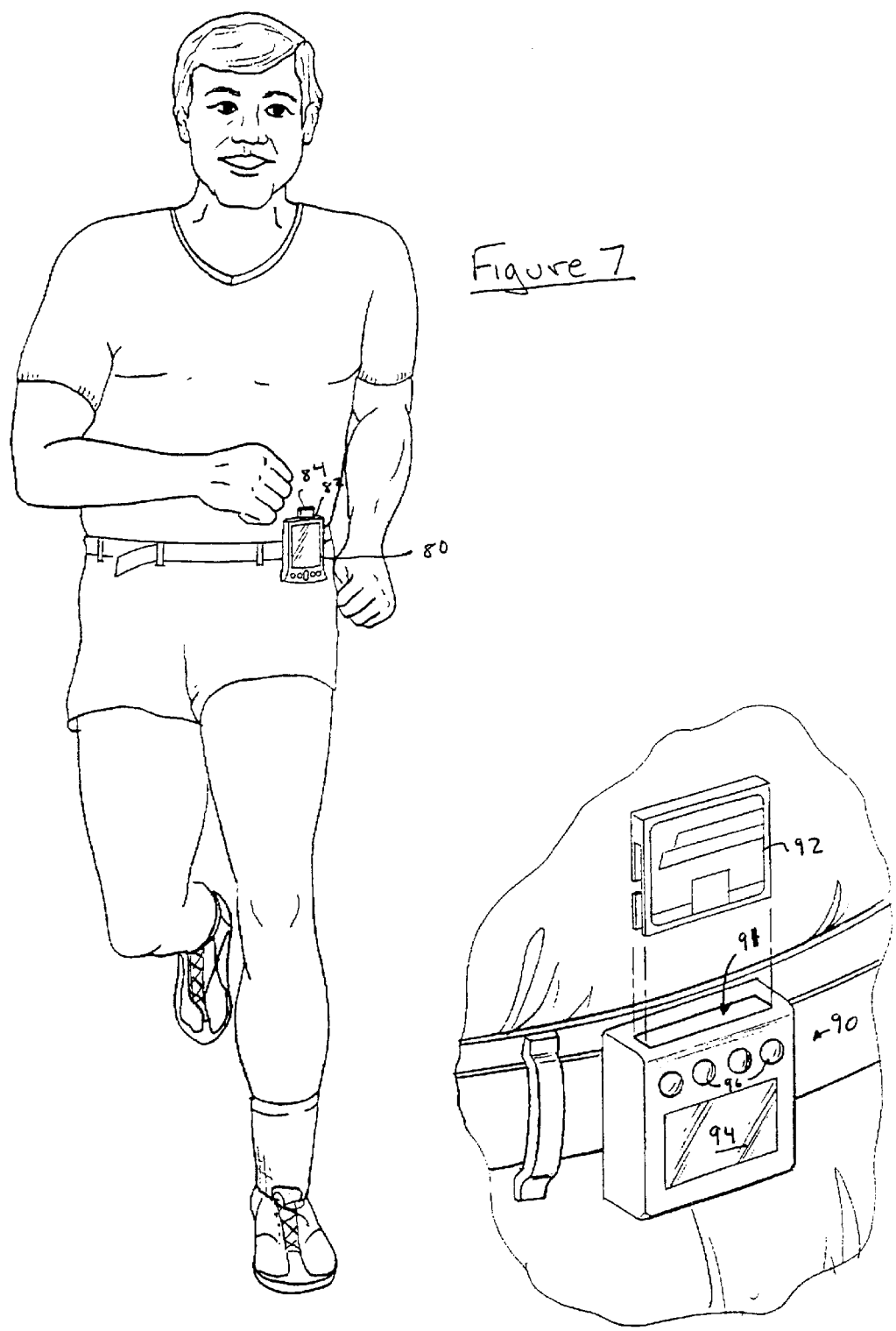
FIG. 7 is a front view of a runner with a PDA strapped to his belt.
FIG. 8 is a perspective view of a pedometer module according to the present invention along with a memory module.

Referring now to FIG. 7, a pedometer module according to the present invention will be discussed. A runner is shown in FIG. 7 with a PDA 80 strapped to his belt. As with the earlier discussed embodiments, the PDA includes an accessory slot 82 on its upper side. A pedometer module 84 is docked into the PDA. In alternative embodiments, the module may grip the PDA's housing or the module and PDA may interconnect in any other way. The pedometer module 84 may work on any of the principals currently used for pedometers, such as a one, two, or three-axis accelerometer for measuring acceleration in various directions, a pendulum for detecting motion, or a piezoelectric sensor for detecting motion. The pedometer module communicates motion or acceleration information to the PDA where it is processed to determine the motion being experienced by the PDA. From this information, a reasonable approximation of running distance, running speed, and other exercise factors may be determined.

In its simplest version, the pedometer module 84 merely includes the accelerometer or motion sensor, sufficient electronics to buffer and/or condition a signal from the accelerometer, and electrical contacts for mating with the contacts in the accessory slot of the PDA. In a more complex embodiment, the pedometer module 84 may also include processing circuitry for further processing the signal from the accelerometer. The module may include memory, which may include application software for use by the PDA when the pedometer module is plugged into the PDA. In this embodiment, the user plugs the pedometer module 84 into the PDA 80 causing the PDA to recognize the presence of the pedometer module and to load the appropriate software either from memory or from the module. The PDA may then display instructions on how to use the pedometer including which buttons operate -which functions. The user then follows the instructions to operate the pedometer module and performs an exercise. During this time, the PDA stores exercise information received from the pedometer module and calculates various exercise parameters such as calories burned, distance covered, average speed, etc. The PDA may use this information for a variety of purposes, such as feedback to the user, entry into an exercise log, or as part of an overall health or fitness program. As another alternative, the PDA may have a built in capability to measure acceleration or movement such that a pedometer module including an accelerometer is not necessary. Movement or acceleration may also be determined in other ways, such as using GPS signals (as described in co-pending provisional patent application Ser. No. 60/179,882), cellular phone signals, radio telemetry, and other approaches. The hardware necessary for determination of acceleration or movement may be incorporated into a PDA or provided as a module that docks with or communicates with the PDA.

Referring to FIG. 8, a second embodiment of a pedometer module according to the present invention is generally shown at 90. In this embodiment, the pedometer module 90 does not directly interconnect with a PDA, but instead includes an accessory slot 91 that accepts a memory module 92. During or after exercise, data from the pedometer module 90 is stored in the memory module 92, which is later plugged into an accessory slot in the PDA for transfer of data. As with earlier embodiments of the present invention, the memory module may include additional capabilities such as processing power and/or application software and updates. In the embodiment of FIG. 8, the pedometer module includes a display 94 and controls 96 such that it may be used as a stand-alone unit. In this case, the memory module 92 merely serves to transfer data from the pedometer to the PDA or other computing device. Alternatively, the pedometer module may be a very simple device that merely records acceleration data onto the memory module for later analysis by another computing device such as a PDA. In this case, it is necessary for the user to first transfer the memory module to the PDA in order to determine their exercise parameters.

Figure 9:
FIG. 9 is a front view of a portion of a runner with another embodiment of a pedometer module shown attached to the runner's chest.
Figure 10:
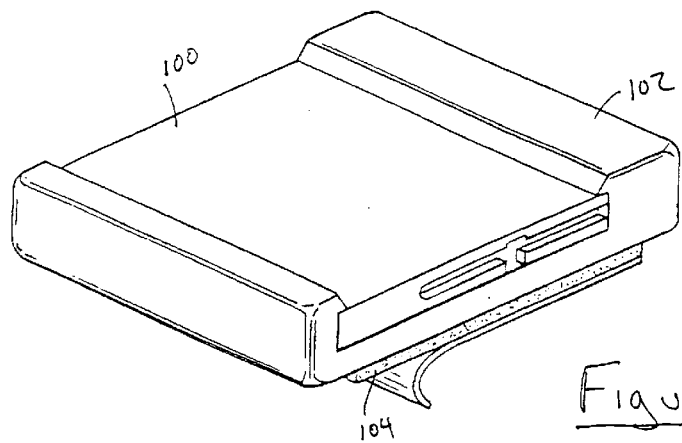
FIG. 10 is a perspective view of a pedometer module supported in a support clip.

Referring now to FIGS. 9 and 10, an additional embodiment of a pedometer module according to the present invention is generally shown at 100. In this embodiment, the pedometer module 100 takes the form factor of a memory module such as those previously discussed. That is, the entire pedometer module is the size and shape of a memory module such that, when not in use, the pedometer module may be detached from the user's body and inserted into an accessory slot in a PDA. The pedometer module includes at least an accelerometer or motion sensor and storage means for storing data produced by the sensor. It may also include conditioning and processing circuitry.

The pedometer module 100 may be attached to the user's body or clothing in any of a variety of ways. According to one preferred embodiment, the pedometer module 100 may be supported in a holder clip 102 as shown in FIG. 10. The holder clip 102 is generally C-shaped and grips the module 100. The module 100 may be inserted into the clip 102 and then removed after use. The clip may be reusable or disposable. The clip 102, as illustrated in FIG. 10, includes an adhesive strip 104 on its under side for attaching the clip 102 to a surface, such as skin or clothing. As will be clear to those of skill in the art, support clips of other designs may be provided. For example, a variety of clips may be provided including other attachment means such as hook and loop fasteners, a spring clip, or a pin. Other clips may include attachment straps for wrapping around an arm, leg, chest, or waist, or may include a slot or clip for interconnecting with another strap. A suction cup-type device may also be used for an application where the clip is to be attached to a smooth surface. As a further alternative, the pedometer module may be attached to, inserted into, or incorporated into other equipment. For example, the module may be inserted into or attached to the runner's shoes, such as by placing it in a slot in the shoe sole. A pedometer module may be incorporated into a music device, a piece of clothing, eyeglasses, or any other piece of equipment. As yet another alternative, adhesive strips may be provided for directly attaching the module to a surface, without the need for the clip 102. The strips may adhesively attach to the module 100 on one side and have adhesive, hook and loop fastening, a pin, or other attachment means on its other side.

After attaching the pedometer module to their body, clothing or equipment, the user then performs their exercise routine. Upon completion of the exercise routine, the module 100 is inserted into an accessory slot in the PDA. The PDA processes the data from the module and displays exercise parameters. The data may be used to determine a variety of parameters such as distance run, speed, and calories consumed. Some or all of these determinations may require calibration for optimal results. For example, the pedometer may be calibrated for calorie expenditure using a calorimeter or calorimeter module as described in co-pending provisional patent application Ser. Nos. 60/178,979; 60/158,554; and 60/225,101. Also, as described in these applications, the pedometer module may serve as a general activity monitor, to be worn during a variety of activities. The data may also be entered into a variety of exercise fitness logs. In one preferred embodiment, the module includes application software for the PDA such that insertion of the module provides the PDA with the necessary software for processing the data from the module. Alternatively, the pedometer module may include a small display and/or controls for stand alone use. The module may also include a time-keeping device such that the data is time-stamped and exercise speed, duration, and other factors may be determined. The pedometer module may also be attached to other devices. For example, the pedometer module could be attached to the crank arm on a bicycle so that parameters concerning bicycle usage may be determined.

EKG/Heart Sound Module

Figure 11:
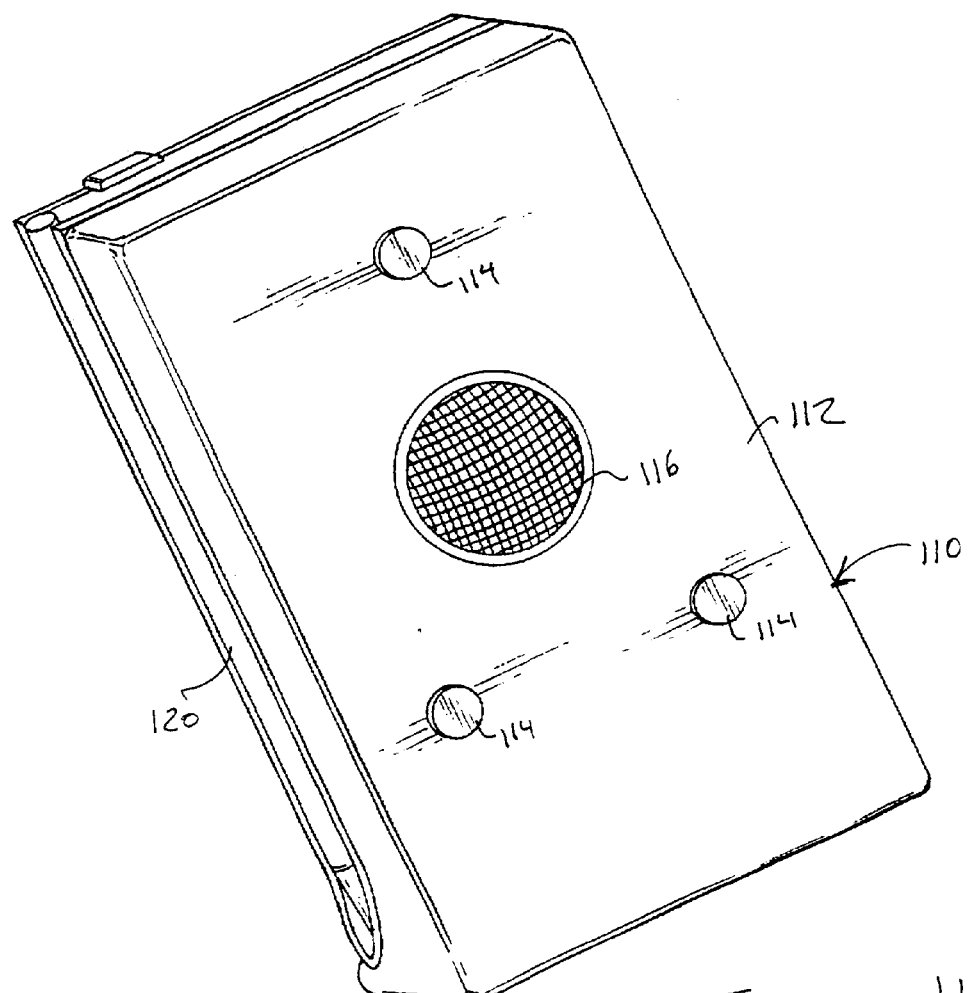
FIG. 11 is a perspective view of a PDA docked with a EKG/heart sound module according to the present invention.
Figure 12:
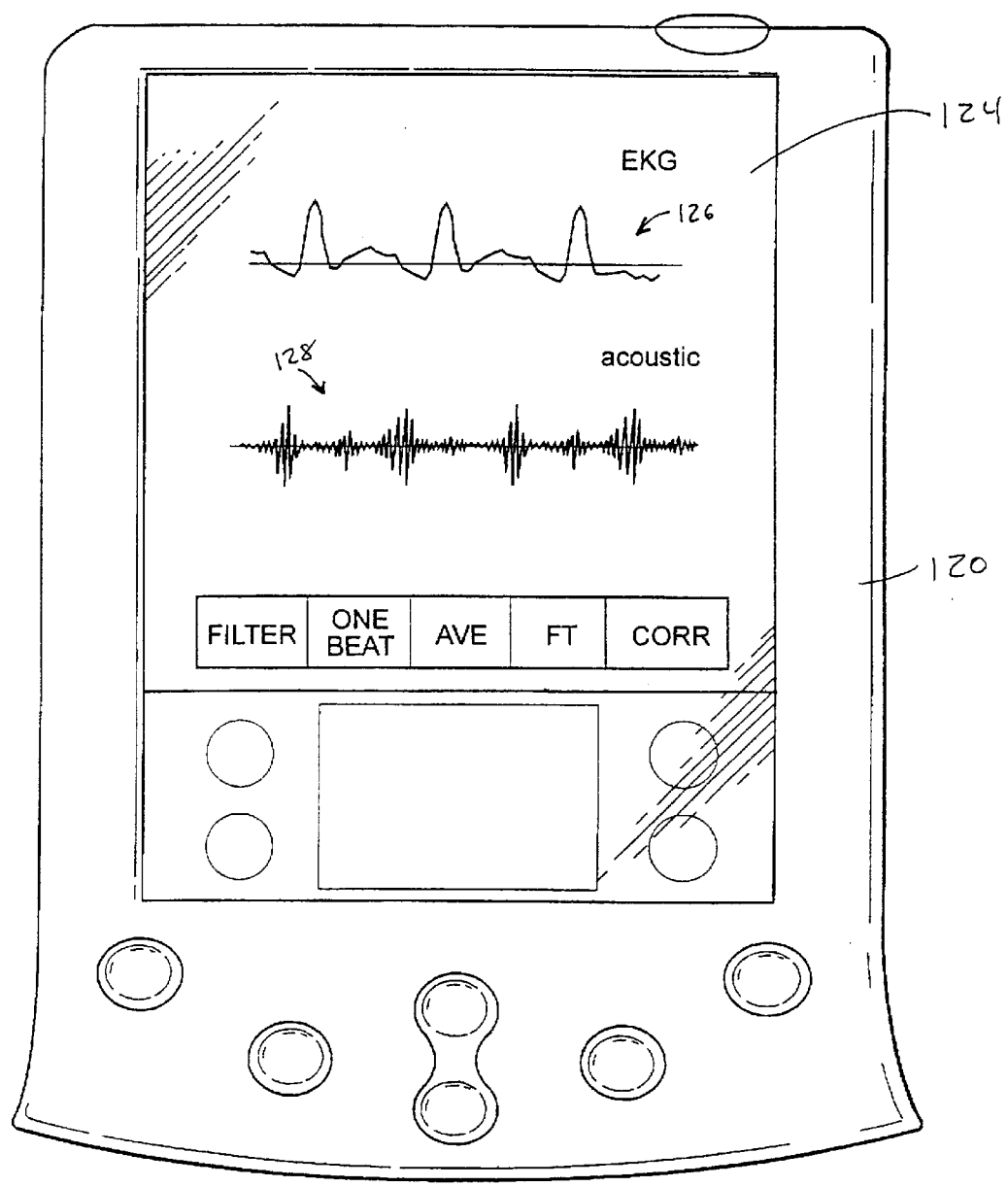
FIG. 12 is a front view of a PDA showing an example of software used with the EKG/heart sound module.

Referring now to FIG. 11, an attachment for a PDA 120 that contacts the chest and records an EKG signal and/or heart sounds is generally shown at 110. There may be a headphone jack on the PDA 120 or on the module for headphones worn by a physician. The PDA may be used for filtering, storing, or other manipulation of the heart sounds or EKG signal.

The module 110 has a housing 112 with electrodes 114 and microphone 116 preferably mounted so as to protrude from the housing. Three electrodes 114 are shown, but any number of electrodes greater than one may be used. Alternatively, one or more of the electrodes may be separable from the module and connected thereto using wires. For example, the module may not include any electrodes on its housing, but instead have several electrodes wired to it so that the electrodes may be placed on the patient while the physician holds the PDA. As another example, one electrode may be on the housing so that it contacts the user's hand and one or more additional electrodes may be placed on the chest.

The module 110 forms an electrical and mechanical interface with the PDA 120 using an electrical connector adapted to match an electrical connection 122 of the PDA 120. Different electrical connectors and docking interfaces may be provided for different PDA designs, as previously discussed.

The microphone 116, which may be supported on the housing or in wired or wireless communication therewith, receives cardiovascular sounds from the person, such as the sounds of heartbeats, the sound of respiration, or a combination of sounds from different sources. The housing 112 of module 110 may contain electronic circuitry, so as to receive, process, and store to memory EKG and microphone signals. For example, the electronic circuitry mounted within the housing may be used to process electrocardiograph data and cardiovascular sound data by converting it into a form suitable for transmission to the PDA, such as using analog to digital circuitry. Memory may be omitted from the module 110, as signals may be transmitted in real time to the PDA for display and/or storage on the PDA. The PDA may also perform the data processing. Either the PDA 120 or module 110 may additionally contain an interface for transferring data to a memory module. As with previous embodiments, communication between the PDA and module may be by wired or wireless transmission, or by the transfer of memory modules, or some combination of these means. Also, the physiological monitor module may, when coupled with the PDA, cause the PDA to recognize its presence and to load appropriate software, or to query the module to identify the module and load software. The software may be stored in the module or on the PDA. The PDA may display or produce instructions for performing a test.

FIG. 11 shows a PDA 120, having a display 124, presenting an electrocardiogram (EKG) 126 and an acoustic signal 128 from the heart. The invention uses the display capabilities and computing capabilities of the PDA to display and analyze cardiac signals from a person. A sound card and speaker, or other sound production system, either built into or an accessory for the PDA, may be used to play back the acoustic signal, or an acoustic interpretation of the EKG.

The PDA may be used to process information, e.g. show frequency components of the heartbeat, perform analog or digital filtering, perform Fourier transforms, construct autocorrelation or cross-correlation data, etc, using software run on the PDA. Acoustic processing may be either hardware or software based. As one example, low frequencies of the acoustic signal, related to valve openings, may be filtered and displayed. High frequencies, such as related to heart murmurs, may also be extracted from the acoustic and/or electrical signals by filtering, and be displayed on the PDA. Monitoring may be in real time, showing heartbeats as they occur, or averages of several heartbeats may be displayed. The data may be recorded to memory and transmitted to a remote device, such as a physician's computer, transmitted to a database or web-site using a communications network, and/or added to medical records such as through a wireless Internet connection, or in other ways.

The invention may be used as a digital stethoscope by a physician. The physician may record the heart data (EKG, phonocardiograms) to a memory module along with a dictated memo about the patient, and other data about the patient. The memory module may then be passed to a secretary for addition to a digital file, electronic record, or database of patient information.

Module 110 may transfer data to the PDA using a wireless transmission method. For example, the module may be held to the chest while data is transferred to the PDA using wireless transmission, with no mechanical association necessary. The module 110 may also contain circuitry for making a wireless Internet connection for data transfer to a remote computer system. The module may have electrical connections so as to connect additional electrodes via wires, in order to improve the EKG signal obtained. Further aspects of the EKG/heart sound module embodiment of the present invention may be understood by reference to co-pending provisional patent application Ser. No. 60/224,651.

Body Fat Measurement Module

Figure 13:
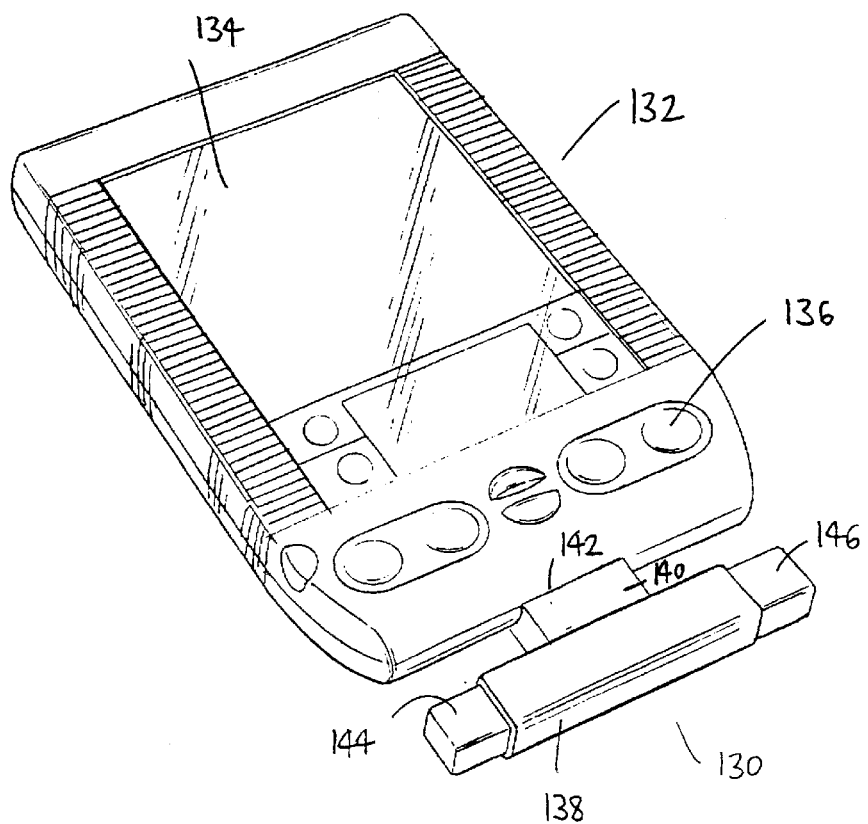
FIG. 13 is a perspective view of a PDA with a body fat measurement module interconnected therewith.
Figure 14:
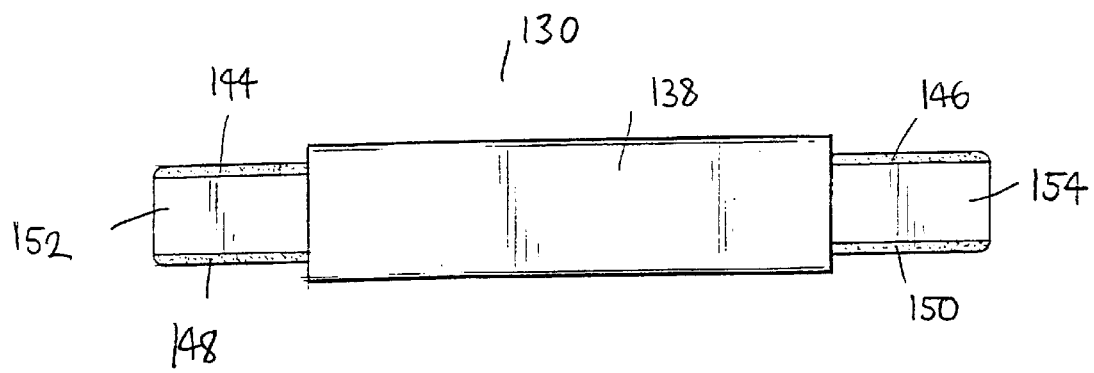
FIG. 14 is an end view of the body fat measurement module of FIG. 13.

FIGS. 13 and 14 illustrate a body fat measurement module shown generally at 130 that plugs into a PDA 132. This module enables body fat or body hydration levels to be determined using bioimpedance. FIG. 13 shows the module 130 plugged into the PDA 132, and FIG. 14 is an end view of the module 130. Referring to FIG. 13, the PDA includes a display 134 and data entry buttons 136. Module 130 has a generally rectangular housing 138 with an attachment flange 140 extending from its upper side. The PDA has an accessory slot 142 in its bottom end. The module 130 mates with the PDA 132 by engaging the attachment flange 140 with the accessory slot 142, thereby providing a physical and electrical interconnection between the module and PDA. Four electrodes 144, 146, 148, and 150 are mounted on electrode supports 152 and 154 protruding from the housing 138, as best shown in FIG. 14. The electrodes are configured so as to form a current electrode pair and sensor electrode pair, and are preferably gripped between the index finger and thumb of each hand. In one embodiment, the current source frequency is fixed in a range from 1 to 100 kilohertz and the voltage is in the range from 1 microvolt to 100 millivolts, with 1 millivolt at 50 kilohertz being one possibility.

A constant current source is connected between the current electrode pair, for example electrodes 144 and 146, and an electric impedance measurement circuit is connected between the sensor electrode pair, for example 148 and 150. Impedance measurement, current source, and data transmission circuitry are contained within the housing 138 to measure bioimpedance, and to transmit the data to the PDA.

For optimally reproducible results, the orientation of the module relative to the hands should be kept the same between measurements. In another embodiment, the current electrodes are the pair 144 and 150, or (equivalently) the pair 148 and 146, so that the current electrodes connect to a finger and thumb of opposite hands. The orientation of the module in the hand is probably less critical in this configuration. Switching circuitry contained within the housing 138 allows the dynamic interchanging of sensor and current electrodes to eliminate any effect of module orientation in the hand, or minor skin conductivity differences between the hands. For example, the current electrode pair could be switched between 144 and 146, 144 and 150, 148 and 146, and 148 and 150 (the sensing electrode pair being formed using the remaining two electrodes in each configuration).

Figures 15, 16:
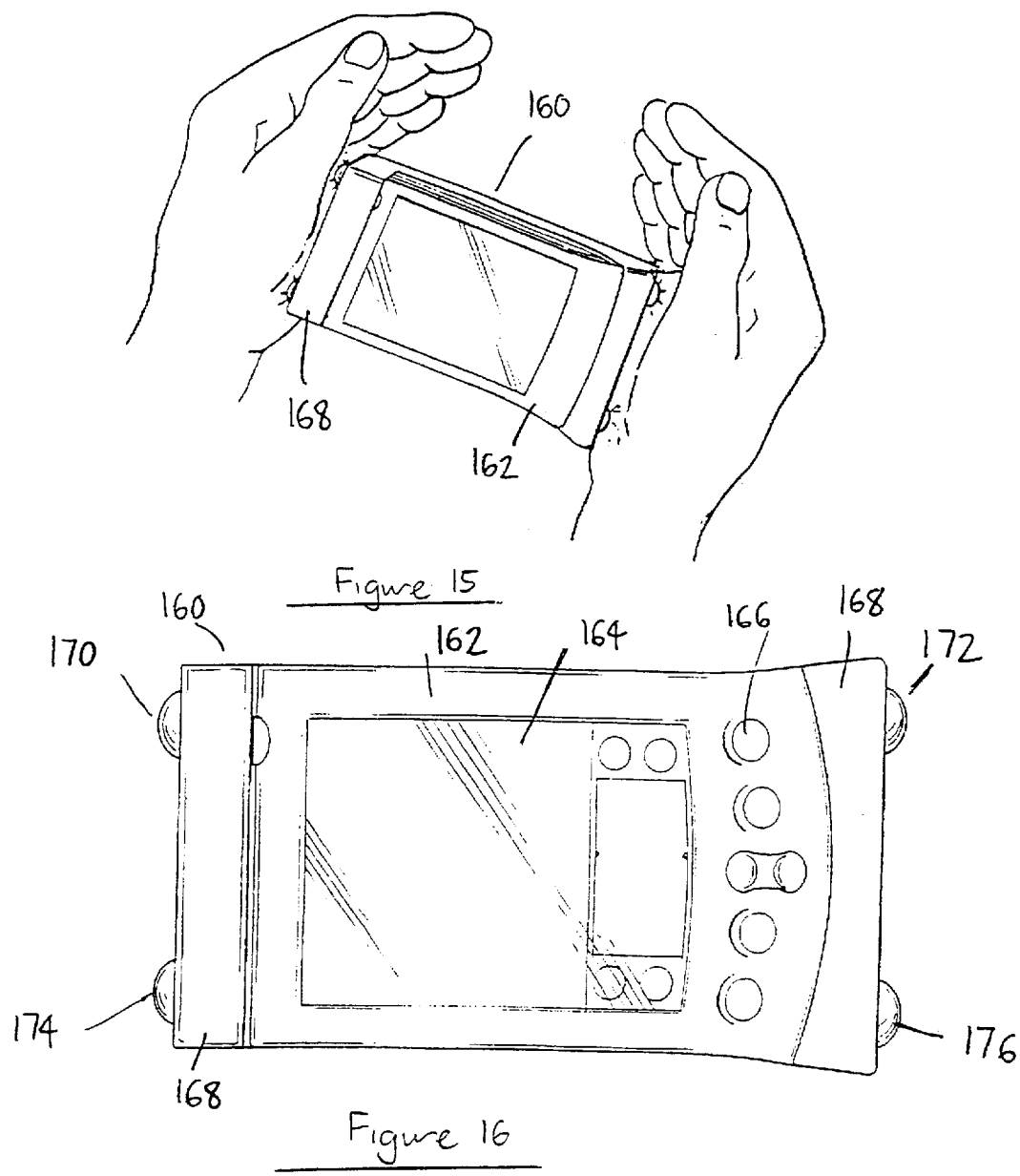
FIG. 15 is a perspective view of another embodiment of a body fat measurement module docked with a PDA and shown grasped between the hands of a user.
FIG. 16 is a front elevational view of the PDA and body fat measurement module of FIG. 15.

FIGS. 15 and 16 show another embodiment of the body fat measurement module. FIG. 15 shows the body fat measuring device, generally at 160, held between the palms of the hands. As shown in FIG. 16, the device 160 comprises a PDA 162 (having a display 164 and data entry buttons 166) docked with a docking interface or frame 168. The frame has surface mounted electrodes 170, 172, 174, and 176. Preferably the frame 168 holds circuitry for bioimpedance measurement between a sensor electrode pair (one on each side of the device, such as 170 and 172), and a constant current source connected to the current electrode pair (such as 174 and 176). Preferably, the device is held so that the sensor electrode pair are those nearest to each other through the body, i.e. the electrodes closer to the wrists when the device is held as shown in FIG. 15. In another embodiment, diametrically opposite electrodes are used as the current electrode pair (e.g. 170 and 176) and sensor electrode pair. In another configuration, switching is used to permutate between electrode combinations to reduce or eliminate the effect of device orientation within the hands. The device may also be placed between the wrists, or between the legs just above the ankles. The data entry capabilities, computing means, memory, and display of the PDA 162 allow data about the person (e.g. height, weight, gender, etc.) to be entered, body fat percentage computed using predictive equations, and displayed to the person. Other embodiments of a body fat module include wired or wireless communication with a PDA, self-contained computation, and transfer or data using a memory module.

As a further alternative, a body fat measurement module may take the form of a module that mates with the back and/or sides of the PDA and includes electrodes positioned along the upper and lower edges of both sides such that a user may grip the electrodes by holding the PDA in a normal position. That is, the user would place a thumb of each hand on the upper edge of the sides of the PDA and a finger of each hand on a lower edge of the corresponding sides, thereby contacting four electrodes. Further aspects of these embodiments of the present invention may be understood by reference to co-pending provisional patent application Ser. No. 60/219,069.

Body fat content, fat free mass, total body water, and body cell mass may be determined from the obtained bioimpedance data (as described in U.S. Pat. No. 5,615,689 to Kotler, incorporated herein by reference). Multiple frequencies may be used to determine the intracellular and extracellular water content of the body. As described in U.S. Pat. No. 4,793,362 to Tedner, frequencies of 1.5 kHz and 150 kHz may be used to determine the fluid balance of a body.

When used to determine body fat, the devices described above assume a certain level of hydration of lean tissue. Body fat data for dehydrated persons will be inaccurate, such as after consumption of alcohol or other diuretics, or after vigorous exercise. However, body fat proportion changes over a much longer time scale than tissue hydration levels, so that the devices described in the above embodiments may also be used to monitor tissue hydration over a short time period (e.g. hours, days) for example as during an exercise program, weight control program, sporting event, as part of another physiological monitoring program (e.g. heart condition monitoring, see U.S. Pat. No. 5,788,643 to Feldman), or during a medical procedure such as dialysis, see U.S. Pat. No. 4,008,712 to Nyboer, or during drug administration, see U.S. Pat. No. 4,880,014 to Zarowitz et al., or for blood pressure monitoring, see U.S. Pat. No. 4,807,638 to Sramek. A PDA may be used as a diet log, and in conjunction with scales and bioimpedance analysis measurements of body hydration, body weight compensated for fluid loss can be calculated and used in a weight control program. The devices described above are also useful for physiological monitoring during exercise or sporting events, in order to determine body hydration levels and the levels of extracellular and intracellular water. Bioimpedance may also be used to determine other parameters. For example, it can be used to determine stroke volume of blood in the chest.

Body Temperature Monitoring Module

For many medical conditions, and for certain aspects of health management, it is beneficial to monitor the body temperature of a patient or individual. According to another embodiment of the present invention, a temperature monitoring module is provided which docks with or otherwise communicates with a PDA. The module, which may be of various sizes and shapes, may be worn for period of time and then plugged into the PDA to transfer data to the PDA. Preferably, the module monitors temperature over time. The PDA may then be used to plot temperature vs. time. The module may contact the skin, or determine temperature in other ways, such as from the ear.

In one preferred embodiment, the temperature monitor module includes wireless communication capability and wirelessly transmits temperature data to a PDA located within the wireless range. Software on the PDA monitors the temperature and signals a user if attention is required. For example, the temperature module may be placed on a sick child and the parent can carry the PDA around the house or keep it in their room. If the child's temperature rises too high, or the temperature curve over time indicates a problem, the parent can be signaled. The PDA may include software that makes recommendations as to how to treat the conditions. The PDA may also communicate with a remote computer or health professional to obtain appropriate feedback. This embodiment of the present invention may also be used with other physiological monitors, such as to monitor perspiration bed-wetting, respiration, heart rate, etc.

The PDA and/or temperature monitor module preferably includes a real time clock, either as part of its operating system or in the application program for the thermometer. The system records the time of measurement of the various thermometer readings for use in plotting a graph of the subject's temperature over a time period such as a day or a week.

A variety of transducers exist which are adapted to be attached to the body of the patient, usually an infant, so as to sense the body temperature, generate an electrical signal proportional to the temperature and transmit some form of wireless signal embodying the temperature information. This signal may be sent continuously or at regular intervals based upon a clock contained in the unit or measurements may be triggered by a remotely transmitted signal. A wireless communication module may be docked with the PDA to allow it to wirelessly communicate with the temperature monitor and/or remote computers.

Figure 17:
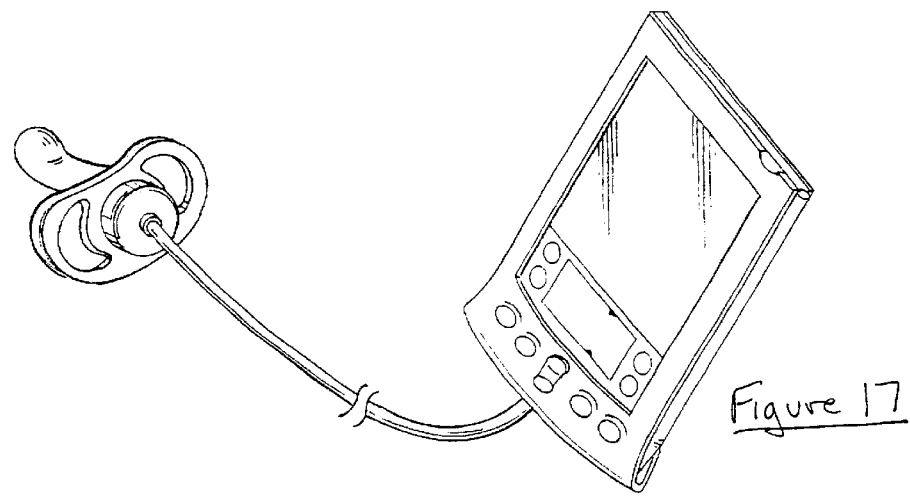
FIG. 17 is a perspective view of a PDA with a pacifier-based body temperature module.
Figure 18:
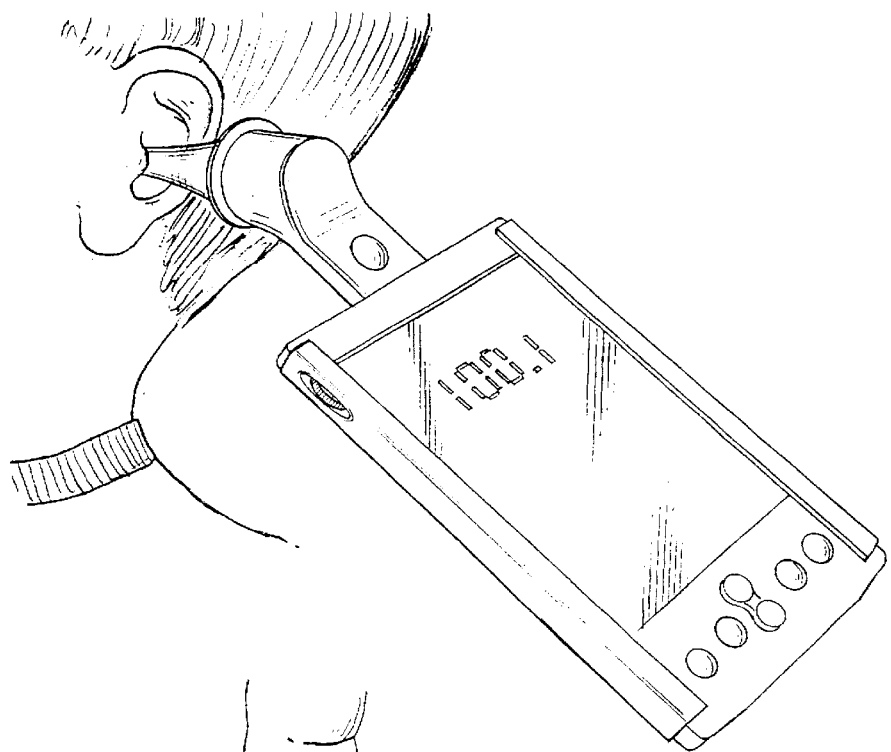
FIG. 18 is a perspective view of a PDA with an ear canal body temperature measurement module according to the present invention.

The temperature transducer and transmitter may be attached to a portion of the monitored subject's body by an adhesive such a band aid-type device. Alternatively, the transducer and transmitter could be incorporated in an armband, headband or the like, or in a body garment to be worn by the subject. Typically these temperature monitors are used with infants and the temperature transducer and transmitter could be incorporated in a pacifier adapted to be supported in the mouth of the infant, as shown in FIG. 17. The pacifier module is illustrated as wired to the PDA, but may wirelessly communicate. FIG. 18 shows another embodiment in which an ear canal temperature measurement module interconnects with a PDA. Once again, the module may wirelessly communicate, use memory modules, store data for later analysis, etc. Other designs for temperature monitor modules include thermometer shaped probes and contact based measurement devices.

The temperature monitor module preferably incorporates a temperature responsive circuit device such as a thermistor, or temperature responsive transistor which could be incorporated in an oscillator or the like to generate a temperature dependent electrical signal for transmission to the PDA.

After the PDA processes the temperature signals, it may periodically transmit them to a remote site such as a web site on the Internet. The web site could maintain a record of the patient's temperature along with other health related data. It could be accessed by a health care professional or the information on the web site could be automatically transmitted to a terminal available to the health care professional or a PDA carried by the health care professional. The health care professional could transmit treatment recommendations back to the patient associated PDA via the Internet or other public networks.

According to an alternative embodiment, a temperature monitor module may be used along with a baby monitor such that temperature data is transmitted to the monitor along with sounds or video. Further aspects of temperature monitoring may be understood by reference to co-pending provisional patent application Ser. No. 60/177,011.

Blood Pressure Module

Figure 19:
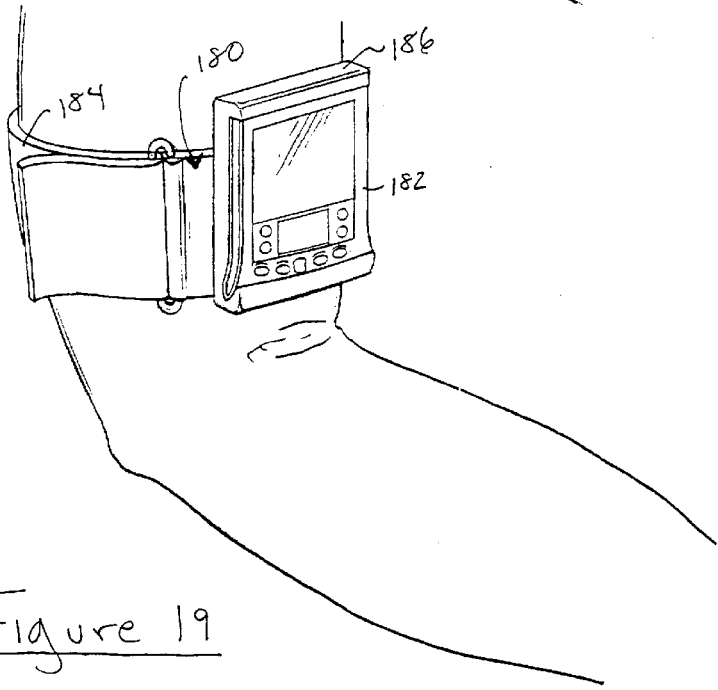
FIG. 19 is a perspective view of a PDA docked with a blood pressure measurement module according to the present invention.

For some medical conditions, especially cardiac and pulmonary conditions, it is beneficial to monitor blood pressure. Blood pressure can be determined at intermittent intervals using various available technologies, such as an automatically inflating cuff and associated mechanisms. A ring or wristwatch-like cuff based device may be used as well. Also, bioimpedance modules can be used to monitor blood pressure, as described by Sramek in U.S. Pat. No. 4,807,638. FIG. 19 illustrates a first embodiment of a blood pressure module 180 for use with a PDA 182. The blood pressure module includes a cuff 184 to be wrapped around a patient's arm and associated mechanism to inflate the cuff and determine blood pressure. The blood pressure module 180 according to the present invention includes a docking interface 186 for the PDA 182. As with the earlier described monitor modules, the PDA 182 may provide some of the necessary controls, display, and processing, or the module 180 may work without the PDA with the PDA later being docked for data transfer and/or processing. Wired, wireless, or memory module based transfer of data are also possible.

According to another embodiment, the blood pressure module is in the form of a ring worn over a finger or toe. Preferably, blood pressure readings are taken periodically and transferred to a PDA. In yet another embodiment, a wrist mounted device has a band having a section of electrometric material. The electrical conductivity of the band may be modulated by a pulse through the wrist. Each of the alternatives described with respect to earlier embodiments also apply to the blood pressure module.

Blood Oxygenation Module

Figure 20:
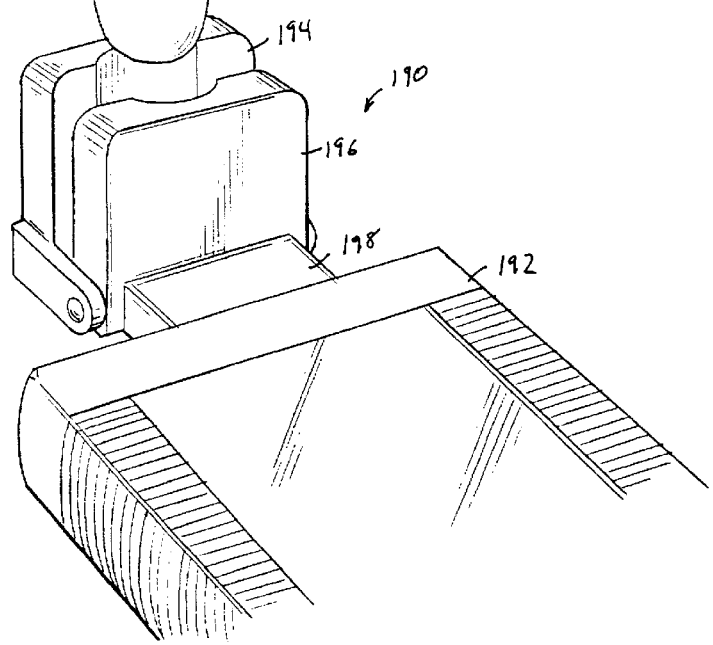
FIG. 20 is a perspective view of a PDA with a pulse oximeter module according to the present invention.

Referring now to FIG. 20, a pulse oximeter module is shown generally at 190 clipped to a person's finger. Radiation from sources within the oximeter are transmitted through the finger, or reflected from finger tissue, and subsequently detected by a radiation detector. The wavelengths are chosen for strong oxyhemoglobin and deoxyhemoglobin absorption. Conventionally, a red light emitting diode (LED) and an IR LED are used as radiation sources, however other wavelengths such as blue (for deoxyhemoglobin absorption) may be used, and semiconductor lasers are also useful. Blood oxygenation, and other blood compositional information, can be determined from transmission or reflection at different wavelengths. As shown in FIG. 20, the pulse oximeter module 190 plugs into the accessory slot in a PDA 192. The module 190 includes an upper member 194 and a lower member 196 that are connected by a hinge such that a finger may be gripped between the members 194 and 196. An attachment flange 198 extends from the lower member 196 for physical and electrical interconnection with the PDA 192. Alternatively, the module may be interconnected with the PDA by a wired or wireless connection. Memory modules may also be used. The determined blood oxygenation and pulse rate may transmitted from the oximeter to the PDA for processing and use in software programs.

An oximeter in the form factor of a memory module may be placed against the skin. In this embodiment, the module contains radiation sources and a radiation detector, so as to determine the properties of radiation reflected from tissue. Pulse rate and blood oxygenation may be determined from fluctuations in the reflection, and the data stored to memory within the housing of the oximeter. At some convenient time, the oximeter may be removed from the skin and plugged into a PDA for display and analysis of the data.

The PDA may be adapted so as to have an imaging capability. Reflection imaging of part of the skin at two or more wavelengths (e.g. red and blue) can also be used to determine blood oxygenation. The spectral properties of incident radiation may be determined using direct detection such as through a diffuser, or reflection from a standard reflector such as white paper. This method may not be accurately repeatable from one person to another, but as the PDA will generally be used by a single person, the imaging method may be calibrated for a particular body part (such as the palm or finger) for a particular person. If multiple persons are using the PDA, each may be provided with a log-in identification. The PDA or an accessory may provide the radiation for reflection oximetry of a skin part.

The oximeter module may be used as part of a system for medical diagnosis of conditions such as heart disease and emphysema. The system may assist the person in requesting medical assistance, or assist a physician in treating the person. A physician may have their own PDA, which interacts with various modules associated with different patients. The modules may communicate patient identification data along with other data to the physician's PDA. The physician may access patient records through the PDA, and update them, via a communications link.

As a further alternative, a sensor array may be used to image the retina, and colorimetry of the retinal image used to determine blood oxygenation. A color reference channel may be provided for improved quantitative measurements. A wrist-mounted module may extract blood for characterization. The module may be removed and connected to the PDA, or the PDA may connect to the module and be worn.

Heart Rate Monitor

In addition to several of the techniques described above in relation to blood oxygenation, pulse rates may be determined using a number of other methods. For example, a sensor may have the physical form of a memory card, be mounted on the skin of the person, monitor data related to heart activity, and store the raw or processed data to memory. The sensor may then be removed and plugged into a PDA for transfer and analysis of data. A skin-mounted sensor may contain ultrasonic transducers sensitive to the motion of blood through tissue. A chest mounted heart activity monitor may have a microphone so as to record the noise of heartbeats, from which pulse rate may be determined. The skin mounted monitor may also contain a temperature sensor, as body temperature and pulse rate together have been shown to correlate with metabolic rate, and hence are useful to record within a calorie management system. A micromachined activity sensor may also be included within the heart activity monitor, such a device would then be very useful within a physical fitness program, a cardiac rehabilitation program, a calorie management system, a weight loss program, a cardiac problem diagnosis scheme, or other medical or lifestyle related activity.

Pulse rate as well as blood oxygenation may also be determined using wrist or finger mounted devices, such as a ring. Modulation of reflected or transmitted radiation may be monitored using built in radiation sources and detectors. The expansion of a band due to the pulse may be detected using strain detecting materials, e.g. elastomers having changing electrical properties under strain.

The heart rate interval (HRI) may also be determined and used to estimate stress levels of the person. Pulse rate and HRI may be correlated with metabolic rate, and used in a calorie management system. Data may also be used to assist decision making by the person, such as lifestyle, diet, or medication adjustments. The PDA may provide or control a biofeedback mechanism to assist in calming the person. HRI may be tracked during the determination of resting metabolic rate using an indirect calorimeter and used to help determine when a person is fully relaxed. Monitored HRI values may also be used in any algorithm used to obtain an accurate resting metabolic rate from respiratory or other data which changes with time as a person relaxes.

Blood Glucose Module

Figure 21:
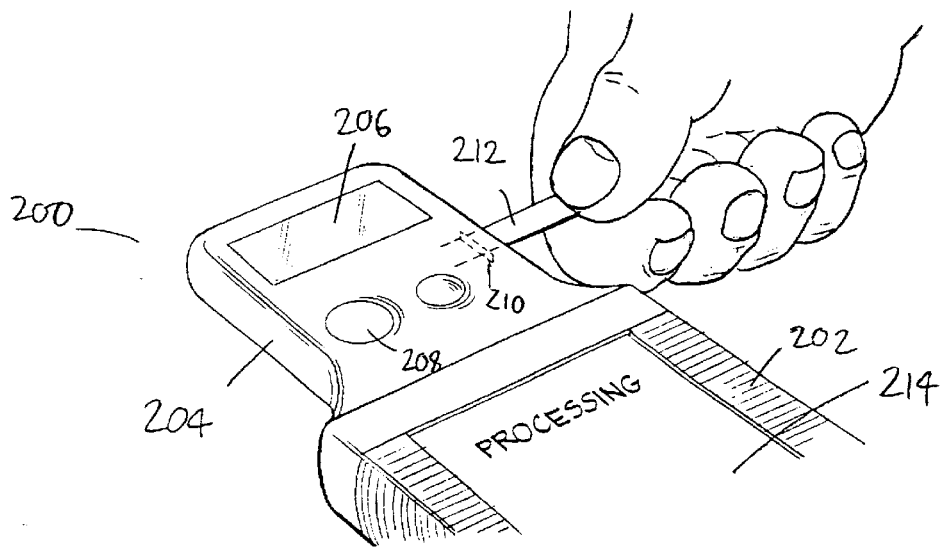
FIG. 21 is a perspective view of a portion of a PDA with a blood glucose module docked therewith.

FIG. 21 shows a blood glucose reader module shown generally at 200 that plugs into a PDA 202. The module 200 has a housing 204 that mates with the PDA 202 by engaging an accessory slot (not shown) in the upper end of the PDA. The module housing 204 has a slot 210 configured so as to receive a standard blood glucose test strip 212. Blood glucose levels can be determined using a test strip onto which a drop of blood is placed. After drawing blood and preparing the test strip in a conventional way, the person places the test strip 212 into slot 210 in the module 200. A numerical value for blood glucose level is determined using radiation emission and detection circuitry within the housing 204 of the module 200, for example using colorimetry. This blood glucose number is then transmitted to the PDA. The number can be displayed on the PDA display 214.

Software running on the PDA may be used to display graphs of blood glucose versus time. In combination with diet logging software, the glycemic response of the person to various foods may be determined. Software may be built into the module, and be automatically loaded onto the PDA and initiated when the module is docked with the PDA. A glycemic model for the person may be developed, and refined with each blood glucose measurement, so as to allow prediction of future levels of blood glucose. Glyosylated hemoglobin and related compounds may also be monitored to determine average blood glucose levels, for comparison with values calculated using the model and for model refinement. The test strip reader module may also contain memory to record data, and may possess a numerical display 206 for displaying determined blood glucose levels, and buttons 208 to initiate operation, so that the module can work in a stand alone mode. The display 206 and buttons 208 may be omitted, as functional elements of the PDA (such as display 214 and conventional data entry buttons) may be used to operate and display results obtained from the module.

A finger may also be placed on or in a module docked with the PDA. Fluid, such as blood or interstitial fluid, may then be extracted by any convenient method, such as manual lancing (before placing the finger), automatic lancing, or other mechanical methods, microcapillary insertion, other capillary methods, reverse iontophoresis, osmosis, or other method. The extracted fluid may then be analyzed for blood glucose concentration, for example by monitoring enzymatic reactions, spectroscopy, or fluorescence quenching. Alternatively, radiation sources such as semiconductor lasers may be used in the non-invasive analysis of tissue fluids for the determination of blood glucose. A blood glucose monitor may also be implanted into the body, for example as described by Colvin et al. in international application WO 00/13003. An implanted sensor may communicate using wireless methods to a PDA. The implanted sensor may also be powered by radiation (radio, IR, other electromagnetic radiation, or ultrasound) emitted by the PDA or from other sources.

The PDA may be used to provide decision support to the user. An entire diabetes management system can be provided based on the PDA. Blood glucose data, diet log records, and an automated insulin pump may be used. A single module may serve as a glucose module and include all necessary software for diabetes management, diet tracking, and health management, as well as references such as drug references. The PDA may interact with other commercially available diabetes management devices. Further aspects of these embodiments of the present invention may be understood by reference to co-pending provisional patent application Ser. No. 60/219,070.

Ultra-Sound Sensors

Figure 22:
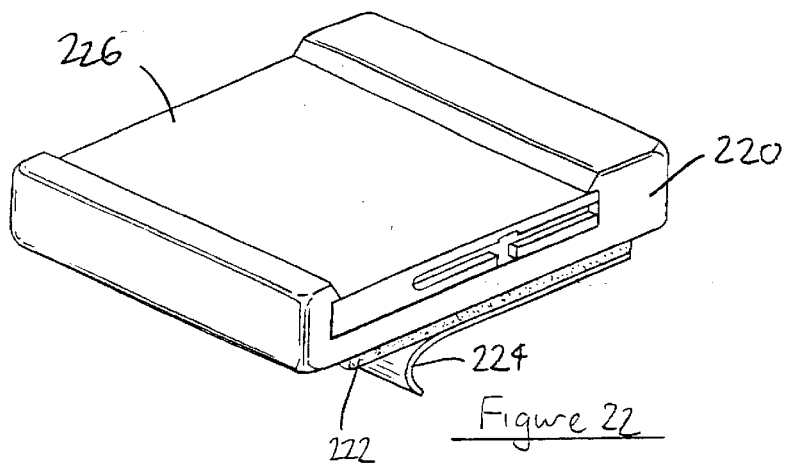
FIG. 22 is a perspective view of an ultrasonic sensor module supported in an accessory clip.

Ultrasound-based sensors have numerous applications in health and fitness management. Ultrasonic sensor modules for use with the present invention may take several forms. FIG. 22 shows a clip 220 having an adhesive layer 222 applied to one face of the clip 220, and a removable release layer 224. The clip is adapted to hold a physiological monitor 226 with the form factor of a memory module, such as a flash memory card. Prior to use, a person peels off the release layer 224, exposing the adhesive layer 220. The clip may then be adhered to the skin of a person using the adhesive layer. In a preferred embodiment, monitor 226 contains one or more micromachined ultrasonic transducers.

Figure 23:
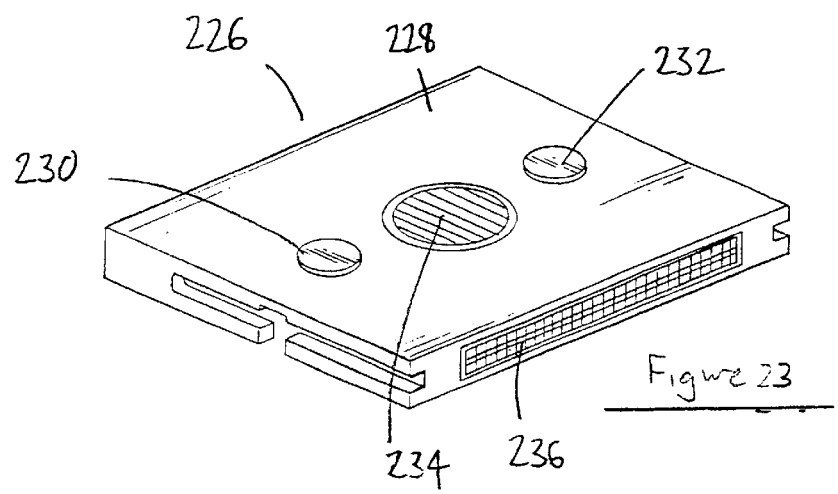
FIG. 23 is a perspective view of an ultrasonic sensor module.

FIG. 23 shows monitor 226 having housing 228, ultrasonic transducers 230 and 232, and additionally a microphone 234. The microphone may be used to record cardiovascular sounds, fetal noises, or other sounds. Other physiological sensors may be included within the housing. The monitor 226 has an electrical interface 236 adapted to form a contact with a PDA or other electronic device. The monitor 226 may be removed from clip 226 adhered on the skin, plugged into a PDA for data download, then returned to the clip. The reproducibility of monitor position on the body is improved due to the use of a clip. The clips may contain gel filled holes allowing better acoustic coupling to the skin. Also, the monitors may be directly adhered to the skin using an adhesive or gel layer.

Figure 24:
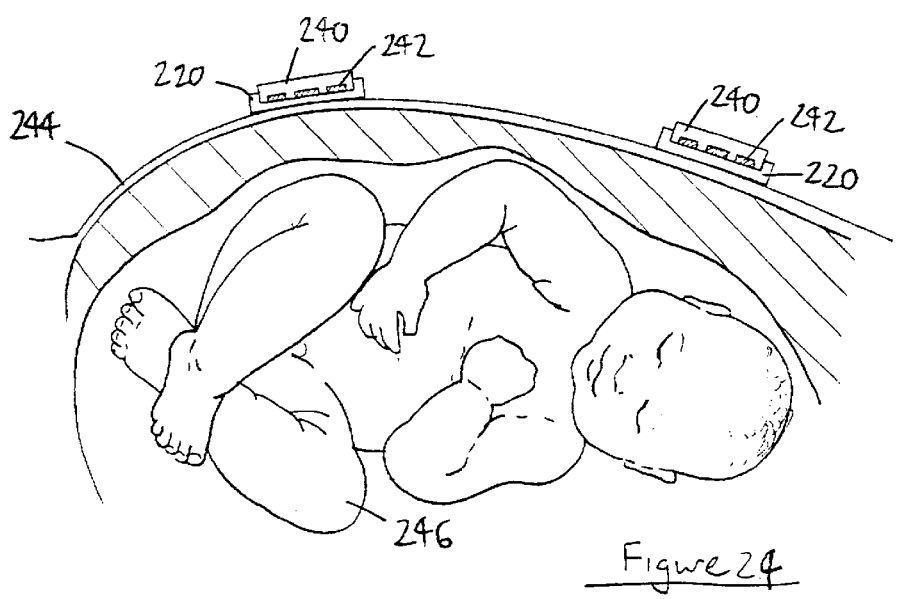
FIG. 24 is a cross-sectional view of a baby in a womb with a pair of ultrasonic sensors shown supported in support clips.

FIG. 24 shows two physiological monitors 240 mounted on the abdomen 244 of a pregnant woman, using clips 220. The distance between the two monitors can be monitored using the transmission and reception of ultrasonic waves by the transducers 242, and used to monitor contractions. Data may be transmitted to a remote monitoring system such as a PDA via Bluetooth® or a wireless Internet connection. The ultrasonic transducers 242 are also used to form images of a baby 246, which may then be displayed on a PDA. A number of such monitors may be used for 2 dimensional or 3 dimensional ultrasonic imaging of the baby. The present invention can also be used in conjunction with the invention described by pending provisional application 60/206,905. The ultrasonic transducers may be used to obtain other data such as fetal heart rate. The monitors may contain memory for storing data, which can be reviewed by plugging the monitor into a PDA. The monitors may also contain wireless communication functionality for real time display of data. Ultrasonic transducers may also be used in a mammography device as described in co-pending provisional patent application Ser. No. 60/205,709.

Figure 25:
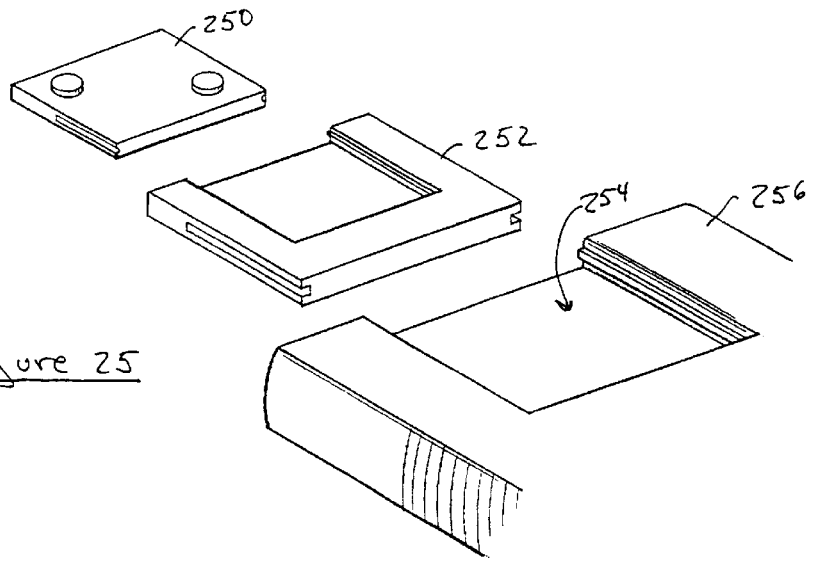
FIG. 25 is a perspective view, partially exploded, showing a portion of a PDA, an adapter, and a physiological monitor module.

As previously discussed, many of the physiological monitoring modules according to the present invention are in the form factor of a memory module such that they may be inserted into a slot in a PDA designed to accept such a memory module. FIG. 25 shows a memory module-type ultrasonic transducer 250 of a somewhat smaller format. Where such a memory module is sized too small, or too large, to fit within the standard opening within a particular PDA, an adapter 252 may be provided which is designed to fit into an accessory slot 254 in the PDA 256. Then, the module 250 is slid into the adapter 252, which is in turn slid into the accessory slot 254. This arrangement may be applied to any arrangement of the present invention.

Skin-mounted monitors such as described may also communicate with sensors embedded in a person's body. For example, they may generate radiation for powering a subcutaneous sensor, and may receive and store data from such a sensor, preferably by wireless methods. Alternatively, an under-skin sensor may have an electrical contact with a clip bonded to the skin of a person, so that the monitor may make electrical contact, via the clip, to the under-skin sensor to read data, power the sensor, etc. The monitor may then be removed from the clip, and plugged into another electronic device for reviewing the data collected by the under-skin sensor.

Skin-mounted ultrasonic transducers may be used to measure chest expansion (e.g. using ultrasonic distance sensors) to obtain an estimate of respiratory intake volume, determine the amount of diaphragm movement, or monitor the posture of the person. Monitors may be placed on the throat or a blood vessel; allowing ultrasonic imaging or quantification of fluid flow rates. The monitor may be used to measure or estimate breath volume or breathing frequency. Ultrasonic monitors, such as described, may be incorporated into a watchband or ring and used to determine pulse rate. For example, a watchband may incorporate an ultrasonic sensor on the upper and lower sides of a wrist so as to pass ultrasonic pulses through the wrist, thereby enabling measurement of pulse rate. Reflection-based measurement, as well as acoustic-based measurement may also be used.

Skin-mounted ultrasonic transducers may also be used to measure bone density. If a low bone density is detected by ultrasound measurements, feedback may be provided via the PDA to the person. For example, the person might be encouraged to consume calcium supplements. Also, bone density may be tracked over time.

Monitors may also contain a physical activity sensor. This may be a motion or acceleration sensor, or may detect physiological changes related to physical activity such as pulse rate and body temperature. The monitor can record physical activity during the day (or over some other time period), then may be removed and plugged into a computer, PDA, or other electronic device (or accessory for the device), so that activity data may be downloaded into the computer, PDA, or other device. This is useful within the context of an exercise, activity and/or weight loss program. It is useful as part of a patient rehabilitation programs. The physical activity sensor may be combined with heart monitoring elements, such as described earlier, as part of a patient rehabilitation program for cardiac patients. Skin-mounted monitors may also contain a combination of electrodes and a microphone for heart monitoring, for example a monitor in the form of 226 shown in FIG. 23, but with electrodes in addition to or replacing transducers 230 and 232.

Food Scale Module

Figure 26:
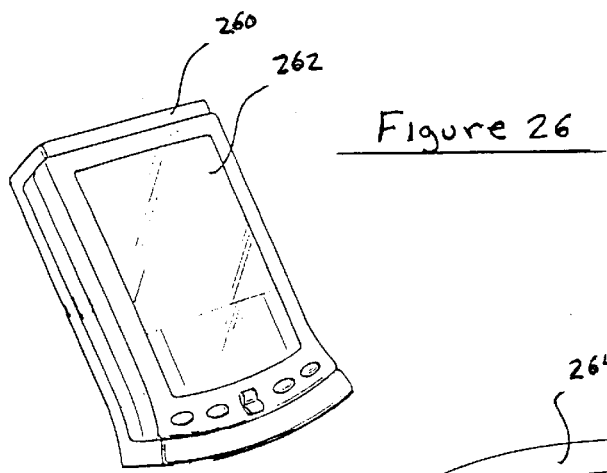
FIG. 26 is a perspective view of a PDA docked with a food scale module.
Figure 27:
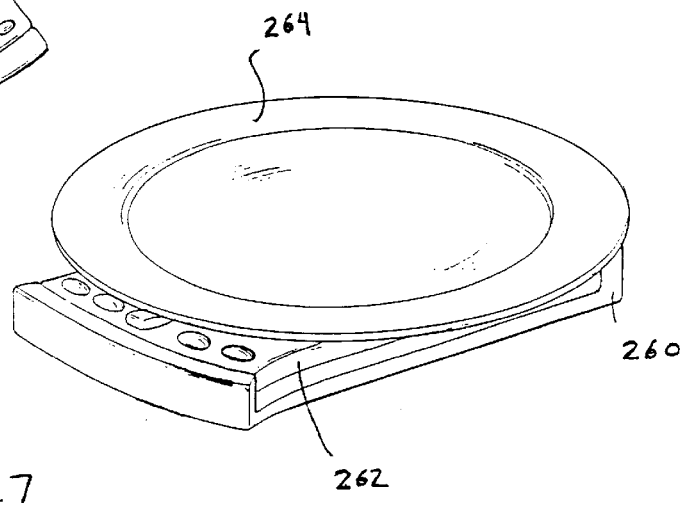
FIG. 27 is a perspective view of the PDA and module of FIG. 26 in a use position.

Weight management and diet control may be assisted by the use of a food scale to measure food portions, as further described in U.S. provisional application entitled "Personal Digital Assistant with Weight Scale Accessory," filed Sept. 22, 2000to Mault. However, many persons do not wish to carry a food scale with them everybody and therefore avoid their use. According to a further aspect of the present invention, a food scale module is provided for use with a PDA. Referring to FIG. 26, a first embodiment of a food scale module is generally shown at 260. The module 260 in this embodiment has a generally C-shaped housing that defines a docking interface for a PDA 262. The module 260 has internal strain gages to measure the force exerted on the housing of the module 260. In use, the module, with the PDA 262 docked therewith, is placed on a surface and an item to be weighed 264 is placed on top of the combination so that the weight of the item presses downwardly on the housing of the module 260, as shown in FIG. 27. As with earlier embodiments, the PDA preferably recognizes the module when it is docked therewith and loads appropriate software either from the module or from the PDA's memory. The information from the strain gages is fed to the PDA where the software uses the information to determine the weight of the item being weighed.

Figure 28:
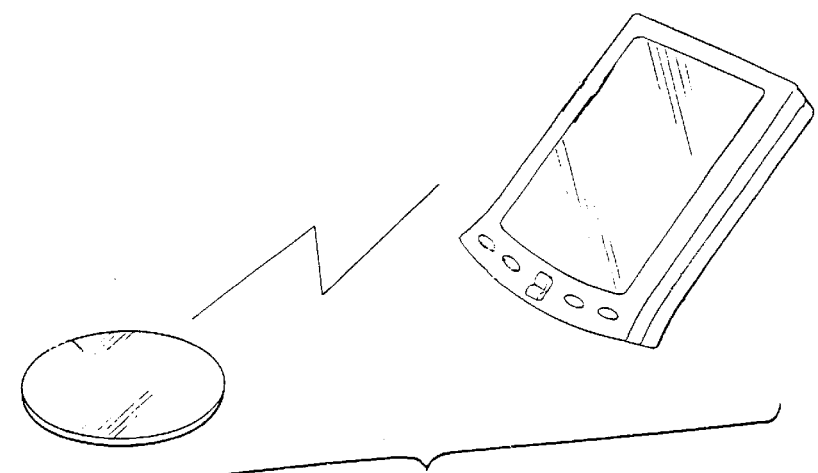
FIG. 28 is a perspective view of an alternative embodiment of a food scale module according to the present invention along with a PDA.

Multiple alternative embodiments of the food scale module are available. Many are described in co-pending provisional patent application, filed Sep. 22, 2000 by Mault, entitled "Personal Digital Assistant with Food Scale Accessory," which is incorporated herein in its entirety by reference. As a first alternative, the module may instead, or in addition, include a hook attachment location so that the module may be held and an item to be weighed may be hung from the hook. As a further alternative, the food scale module may be a stand-alone unit, possibly including controls and a display, which communicates with a PDA by a wired or wireless transmission, or by moving memory modules between the scale and the PDA. The food scale module may also take the form factor of a placemat-like thin material, and may include a docking cradle for a PDA. The food scale may also take the form factor of a coaster- or saucer-shaped disk that communicates with a PDA as shown in FIG. 28. As a further alternative, the food scale module may include recording capability, either video or audio, so that the user may annotate weight scale module or PDA readings with information concerning what was weighed.

Body Weight Scale Module

Figure 29:
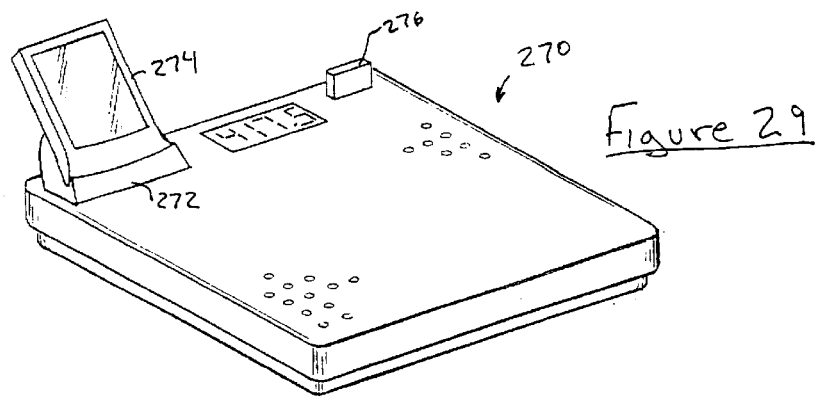
FIG. 29 is a perspective view of a body weight scale module according to the present invention.

Referring now to FIG. 29, a body weight scale module is generally shown at 270. In the illustrated embodiment, the weight scale is similar to standard bathroom scales but includes a docking cradle 272 for a PDA 274. In use, a person first docks their PDA with the weight scale and then steps onto the scale to be weighed. The weight scale may also include a body fat measurement capability according to the methods known to those of skill in the art. After use, the PDA is removed from the docking cradle and the data is stored for use in various software applications. The weight scale may utilize the display, control, and processing circuitry of the PDA, or may have some or all of these capabilities on board. According to alternative embodiments, the scale communicates with the PDA by wired or wireless transmission, or by transferring memory modules 276 therebetween. The weight scale may have both a dock for a PDA and a smart card that is removable, or wired or wireless communication.

Bar Code Scanner Modules

An accessory for the PDA may have the capability for reading bar codes. For example, a module may have the functionality of a memory card and bar-code reader. The module can scan the bar-code, and the UPC code is recorded in memory. This module may also be in the form of a keyring. A miniature camera may be embedded in the bar code module. Image analysis software may be used to extract data from an imaged barcode. A light on the monitor may be used to indicate successful data extraction. Further aspects of this embodiment of the present invention may be understood by reference to a co-pending provisional patent application entitled "Device for Diet Control and Shopping List Generation," filed Sep. 21, 2000 by Mault.

Other Modules

As will be clear to those of skill in the art, other physiological monitors may be incorporated in the present invention. As one example, a bike computer may be constructed as a module for use with a PDA. A docking interface may be designed to mount on the handle bars of a bicycle with a PDA being docked into the docking interface. Various sensors may be provided for sensing bicycle speed and/or physiological parameters such as heart rate, which may be displayed on the display of the PDA. Alternatively, a bike computer may be sized and shaped so as to insert into an accessory slot of a PDA, or a bike computer may include a memory module which may be transferred to a PDA for transfer of data regarding bicycle-based exercise.

As another alternative, a single module may have multiple functions. For example, a heart rate and body temperature module may be combined into a single unit. Also, a heart rate monitor and a pedometer may be combined, such as in a chest strap.

As will be clear to those of skill in the art, any of the alternatives discussed with respect to any of the embodiments of the present invention may be used with any other embodiments, as appropriate. Other alternatives will clear to those of skill in the art. As one example, the memory modules used to transfer data between monitor modules and PDAs may be used with multiple monitor modules and/or PDAs and store data from any and all devices, and thereby serve as a storage device for a variety of health data. As yet another example, the PDAs have been described as having buttons for controlling the PDA and/or monitor modules. However, the may user interact with the PDA using a stylus, voice recognition, a roller-jog selector, a track-ball, an interactive pad, a finger-motion sensor, or any suitable method. As another example, a PDA may be worn or carried by a user and communicate, via wires or wirelessly, with a variety of monitors, such as a pedometer, a heart rate monitor and a temperature monitor. In this way the PDA acts as a command and control center.

We claim:

1. A system for monitoring a physiological condition of the subject, comprising:

- a monitor adapted to measure the physiological condition of the subject, wherein the monitor comprises an EKG and heart sound monitor, the monitor comprising a housing having two or more electrodes disposed thereon and a microphone disposed thereon;
- a handheld unit including a display, a memory, a microprocessor and means for operator control of the handheld unit;
- a two part separable connector, one of the parts fixed to the monitor and the other part fixed to the handheld unit, the two parts being operative, when interconnected, to physically join the monitor and the handheld unit in a rigid manner and being operative to transfer electrical signals from the monitor to the handheld unit for processing by the microprocessor and display of the processed signals on the display of the handheld unit, wherein the electrical signals are correlated with the physiological condition of the subject, so as to provide real time monitoring of the physiological condition; and
- application software supported in the memory of the handheld unit operable to communicate with the monitor and to process electrical signals from the monitor for display.

* * * * *